United States Patent [19]

Beverung, Jr. et al.

[11] E Re. 31,617

[45] Reissued Jun. 26, 1984

[54] OPTIONALLY SUBSTITUTED 1,2,3,5-TETRAHYDROIMIDEZO(2,1-b)-QUINAZOLIN-2-ONES AND 6(H)-1,2,3,4-TETRAHYDROPYIMIDO(2,1-b)QUINAZOLIN-2-ONES

[75] Inventors: Warren N. Beverung, Jr., Cary, N.C.; Richard A. Partyka, Liverpool, N.Y.

[73] Assignee: Bristol-Myers Company, New York, N.Y.

[21] Appl. No.: 421,501

[22] Filed: Sep. 22, 1982

Related U.S. Patent Documents

Reissue of:

[64] Patent No.: 3,932,407
Issued: Jan. 13, 1976
Appl. No.: 521,306
Filed: Nov. 6, 1974

U.S. Applications:

[63] Continuation-in-part of Ser. No. 416,891, Nov. 19, 1973, abandoned, which is a continuation-in-part of Ser. No. 396,638, Sep. 12, 1973, abandoned, which is a continuation-in-part of Ser. No. 291,450, Sep. 22, 1972, abandoned, which is a continuation-in-part of Ser. No. 223,723, Feb. 4, 1972, abandoned.

[51] Int. Cl.[3] ..... C07D 487/04

[52] U.S. Cl. ..... 544/250; 424/251; 544/283; 544/286

[58] Field of Search ..... 544/250

[56] References Cited

U.S. PATENT DOCUMENTS

| | | | |
|---|---|---|---|
| 3,048,587 | 8/1962 | Oroshnik | 544/250 |
| 3,257,401 | 6/1966 | Wagner | 544/250 |
| 3,329,679 | 7/1967 | Sulkowski et al. | 544/250 |
| 3,562,272 | 2/1971 | Pfeffingen | 424/251 |
| 3,563,990 | 2/1971 | Hardtmann | 424/251 |
| 3,594,376 | 7/1971 | Bell et al. | 424/251 |
| 3,598,823 | 8/1971 | Hardtmann | 544/250 |
| 3,600,390 | 8/1971 | Sherlock | 544/250 |
| 3,621,025 | 11/1971 | Jen | 544/250 |
| 3,642,897 | 2/1972 | Hardtmann | 424/251 |
| 3,660,322 | 5/1972 | Bernardi et al. | 424/251 A |
| 3,745,216 | 7/1973 | Jen et al. | 544/250 |
| 3,790,576 | 2/1974 | De Wald | 424/258 |
| 3,833,588 | 9/1974 | Hardtmann | 544/250 |
| 3,859,289 | 1/1975 | Hardtmann | 544/250 |

FOREIGN PATENT DOCUMENTS

| | | | |
|---|---|---|---|
| 2025248 | of 1970 | Fed. Rep. of Germany | 544/250 |
| 2305575 | 2/1973 | Fed. Rep. of Germany | . |

OTHER PUBLICATIONS

Beverung et al.; J. Md. Chem., 18, pp. 224–225, (1975).
Loev et al.; Experientia, 27, p. 875, (1971).
Grout et al.; J. Chem. Soc., p. 3551, (1960).
Lempert et al.; Experientia, 18, 401, (1962).
Hardtmann; Chem. Abstr., 74, 42373g (1971).
Jen et al.; J. Med. Chem., 15, pp. 727–731, (1972).
North et al.; J. Het. Chem., pp. 655–662, (1969).
Simonov et al.; Pharm. Chem. Jour., pp. 4–6, (1969).
Doleschall et al.; Acta. Chemica Acadamiae Scientiarium Hungaricae, 45, pp. 357–368, (1965).
Fleming et al.; Circ. 50: Sup. III, 1148, (1974).
Cox et al.; J. Chem. Soc., pp. 2134–2136 (1970).
Robinson, Ann. Rep. Med. Chem.; Ch. 6, pp. 49–53 (1969).
Born, Proc. Phys. Soc. 162, 67P–68P, (1962).
Evans et al.; J. Exp. Med. 15: 727–731, (1972).
Mustard et al.; J. Lab. and Clin. Med., 64: 548–559, (1964).

*Primary Examiner*—Mary C. Lee
*Attorney, Agent, or Firm*—Fitzpatrick, Cella, Harper & Scinto

[57] ABSTRACT

Optionally substituted 1,2,3,5-tetrahydroimidazol[2,1-b]-quinazolin-2-ones and 6-[H]-1,2,3,4-tetrahydropyrimidol[2,1-b]quinazolin-2-ones or the pharmaceutically acceptable salts thereof are compounds useful as blood platelet anti-aggregative and/or antihypertensive and/or bronchodilator agents in mammals, including humans.

25 Claims, No Drawings

OPTIONALLY SUBSTITUTED 1,2,3,5-TETRAHYDROIMIDEZO(2,1-B)-QUINAZOLIN-2-ONES AND 6(H)-1,2,3,4-TETRAHYDROPYIMIDO(2,1-B)QUINAZOLIN-2-ONES

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation-in-part of co-pending application Ser. No. 416,891, filed Nov. 19, 1973 now abandoned, which is a continuaton-in-part of Ser. No. 396,638, filed Sept. 12, 1973 now abandoned, which is a continuation-in-part of Ser. No. 291,450, filed Sept. 22, 1972 now abandoned, which in turn was a continuation-in-part of application Ser. No. 223,723, filed Feb. 4, 1972 now abandoned.

BACKGROUND OF THE INVENTION

1. Field of the Invention

The compounds of the present invention are useful in the control of mild to severe hypertension, as anti-clotting agents and bronchodilators.

2. Description of the Prior Art

The compounds of the present invention are new and novel. The literature discloses the following prior art:

A. The compounds characterized as 1- and 9-alkyl-2,3-dihydroimidazo-[1,2-a]-benzimidazoles [R. J. North and A. R. Day, J. Hetero. Chem., 655 (1969)]. The compounds have the following structure:

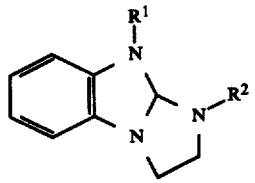

in which $R^1$ and $R^2$ are optionally substituted with alkyl functions.

B. B. Loev, T. Jen and R. A. McLean, Experientia, 27, 875 (1971) diclose the compound having the formula

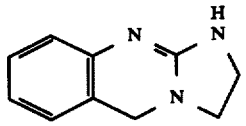

as having potent antihypertensive activity in rats, dogs, cats and rabbits.

C. R. Grout and M. Partridge, J. Chem. Soc., 3551 (1960) report the synthesis of the compound

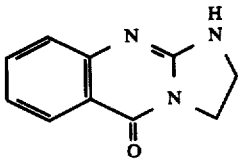

No antihypertensive activity was reported.

D. K. Lempert and G. Doleschall, Experientia, 18, 401 (1962) and Acta Chimica Academiae Scientiarum Hungaricae, 45, 357–68 (1965) report the synthesis of the compounds

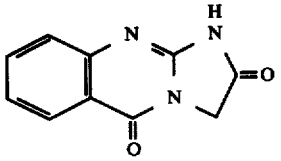

No antihypertensive activity was reported.

E. A. Simonov et al., Khim. Farmatseut, Zh., (1969) [Annual Reports in Medicinal Chemistry, Chapt. 6, 53 (1969)] report the preparation of 9-substituted imidazobenzimidazoles having the formula

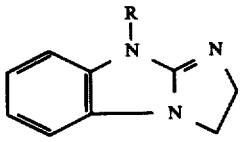

said compounds reported to have hypotensive effects in animals but no detailed data was presented.

F. G. E. Hardtmann, German Patent No. 2,025,248 (1970) reports bronchodilating the hypotensive effects for the compounds having the formula

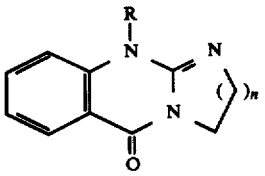

G. T. Jen et al., J. Med. Chem., 15 (7), 727–31 (1972) describe the compounds having the formula

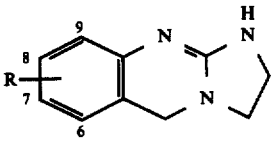

in which R is H, 6-Cl, 7-Cl, 7-MeO, 7-OH, 8-Cl, 9-Cl and 9-$CH_3$ as being hypotensive agents.

SUMMARY OF THE INVENTION

The compounds having the formula

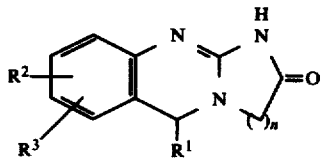

I in which $R^1$ is H, phenyl or (lower)alkyl, $R^2$ and $R^3$ when alike are H, chloro, bromo, fluoro, (lower)alkyl, hydroxy or (lower)alkoxy, $R^2$ and $R^3$ when different are hydrogen, chloro, bromo, fluoro, $SO_3H$, $CF_3$, hydroxy, nitro, amino, phenyl or (lower)alkyl of 1 to 3 carbon atoms or (lower)alkoxy of 1 to 3 carbon atoms, or when taken together $R^2$ and $R^3$ are methylenedioxy or the residue of a phenyl ring, and n is an integer of 1 or 2; or a pharmaceutically acceptable acid addition salt thereof are hypotensive, blood platelet antiaggregative and/or bronchodilator agents.

DETAILED DESCRIPTON

This invention relates to new synthetic compounds of value as hypotensive and blood platelet antiaggregative agents. Most particularly the compounds of the invention are 1,2,3,5-tetrahydroimidazo-[2,1-b]-quinazolin-2-ones having the formula

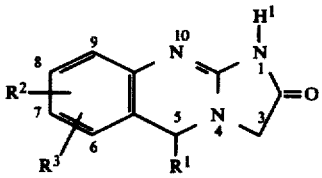

or 6-[H]-1,2,3,4-tetrahydropyrimido-[2,1-b]-quinazolin-2-ones having the formula

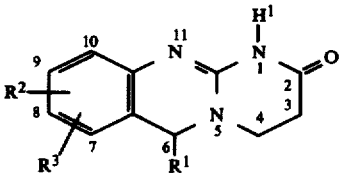

in which $R^1$ is H, phenyl or (lower)alkyl, $R^2$ and $R^3$ when alike are H, chloro, bromo, fluoro, hydroxy or (lower)alkyl of 1 to 3 carbons or (lower)alkoxy of 1 to 3 carbon atoms, $R^2$ and $R^3$ when different are hydrogen, chloro, bromo, fluoro, $CF_3$, $SO_3H$, (lower)-alkyl, hydroxy, nitro, amino, (lower)alkoxy or phenyl, or when taken together $R^2$ and $R^3$ are methylenedioxy or the residue of a phenyl ring; or a pharmaceutically acceptable acid addition salt thereof.

Hypertension is a rather common and serious disease, particularly in elderly people. High blood pressure, a result of hypertension, is a common but serious disease. Most particularly, hypertension is often the cause of crippling or fatal strokes in the elderly. It was therefore an object of the present invention to provide compounds useful in the treatment of mild to severe hypertension.

Subsequent to the preparation of some of the compounds of the present invention, it was found that most of the compounds also possessed unique properties as blood platelet anti-aggregative agents. These compounds are useful in the prevention of intravascular thrombosis, prevention of coronary thrombosis, prevention of transient ischemic episodes, prevention of platelet thrombosis in the use of prosthetic devises (artificial heart valves, etc.). A large number of the compounds of the present invention have also been found to possess desirable bronchodilator activity in mammals.

The objects of the present invention have been achieved by the provision of the compound having the formula

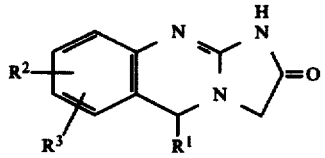

Ia or

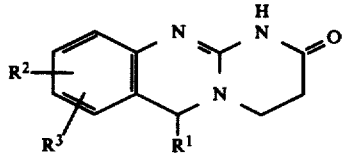

Ib in which $R^1$, $R^2$ and $R^3$ are as defined above.

For the purpose of this disclosure, the compounds of the present invention are represented as having the formulas Ia and Ib. However, compounds Ia and Ib can exist in several possible tautomeric forms, e.g.:

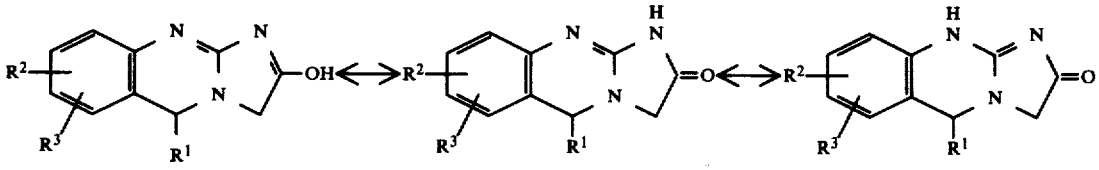

$Ia^2$ Ia $Ia^1$

-continued

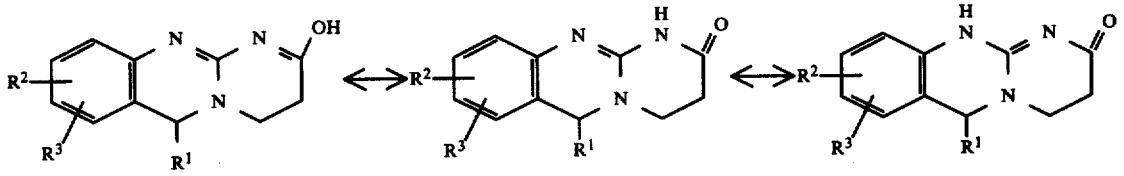

Ib² Ib Ib¹

All the possible tautomers are considered an integral part of the present invention and all these forms are considered included when the compounds are represented as formula Ia or Ib.

Also considered an integral part of this invention are the optical isomers of those compounds having an asymetric center, e.g., (+) and (−)-5,6-dimethyl-1,2,3,5-tetrahydroimidazo[2,1-b]-quinazolin-2-one. The racemic mixture of these compounds are resolved by those methods commonly known in the art.

The nontoxic salts that are pharmaceutically acceptable include the hydrochlorides, hydrobromides, hydroiodides, (lower)alkylsulfates, (lower)-alkyl and aryl sulfonates, phosphates, sulfates, maleates, fumarates, succinates, tartrates, citrates, and other commonly used in the art.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent of the character of the acid used in the preparation of the salt.

Most of the compounds of the present invention can be prepared as shown in Chart I.

Chart I

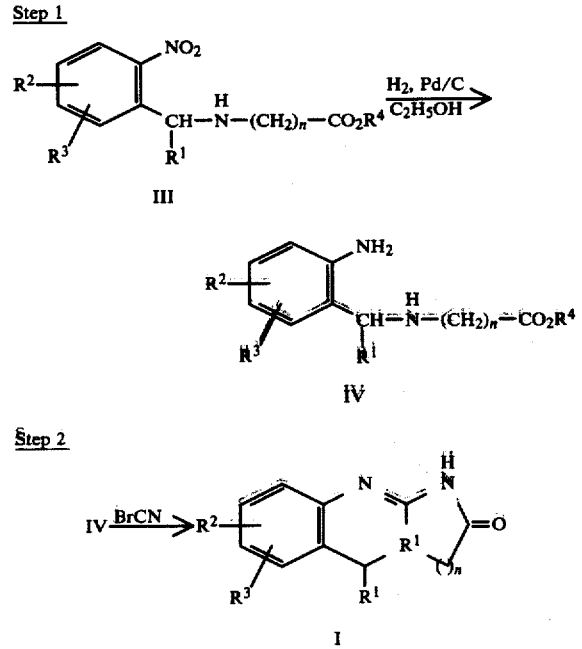

$R^1$, $R^2$ and $R^3$ and n are as defined above and $R^4$ is (lower)alkyl.

In other cases, particularly when $R^2$ or $R^3$ is a bromine or $NO_2$, it may be desirable to brominate or nitrate after producing compound I (see examples).

Two alternative processes for the preparation of the compounds of the instant invention are found in Charts II and III. In some instances, these are the preferred synthetic route.

Chart II

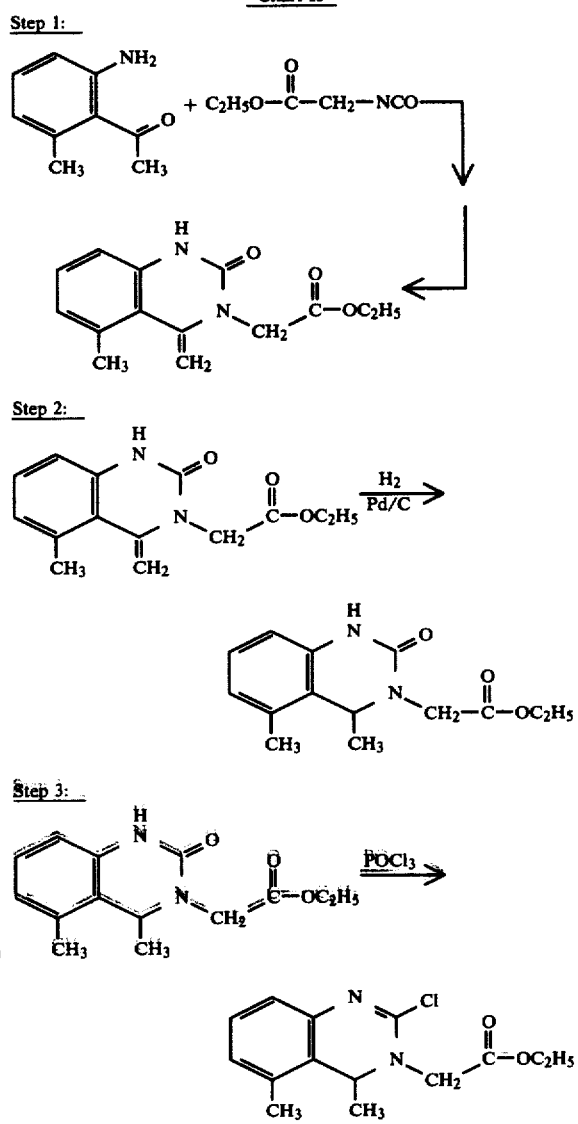

-continued

Chart II

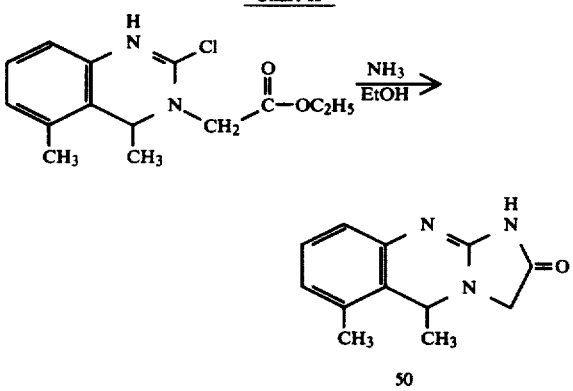

Chart III

Step 1:

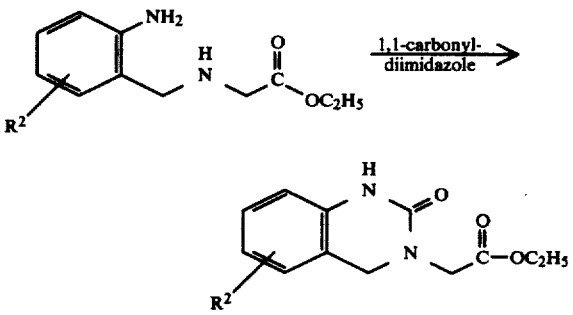

Step 2:

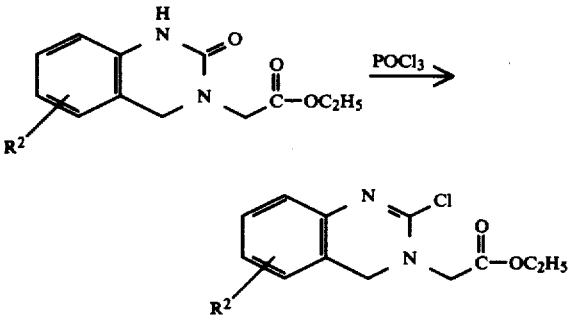

Step 3:

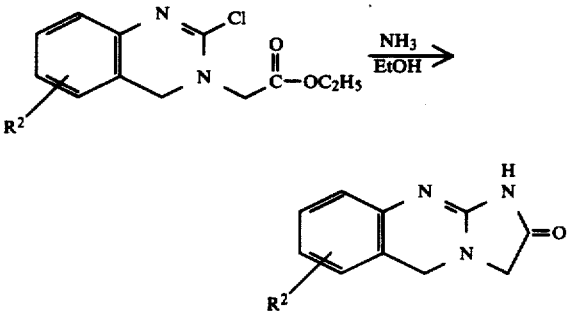

Compounds possessing a substituent at positions 5 and 6 are preferably prepared by the synthetic route illustrated by Chart II.

The objectives of the present invention have been achieved by the provision according to the present invention, of the process for the synthesis of compounds having the formula

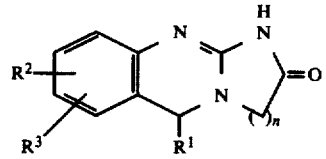

I in which $R^1$ is H, phenyl or (lower)alkyl, $R^2$ and $R^3$ when alike are hydrogen, chloro, bromo, fluoro, hydroxy or (lower)alkyl of 1 to 3 carbon atoms or (lower-)alkoxy of 1 to 3 carbon atoms, $R^2$ and $R^3$ when different are hydrogen, chloro, bromo, fluoro, $CF_3$, $SO_3H$, hydroxy, nitro, amino, phenyl or (lower)alkyl or (lower)alkoxy or when taken together $R^2$ and $R^3$ are methylenedioxy or the residue of a phenyl ring, and n is an integer of 1 or 2; which process comprises the consecutive steps of 1. reducing one mole of compound III, preferably with a noble metal catalyst, particularly 5% palladium on carbon, in the presence of hydrogen under positive pressure until three moles of hydrogen are absorbed, in an organic solvent, preferably a (lower)alkanol such as ethanol, n-propanol, isopropanol and the like to produce a compound having the formula

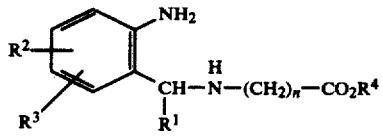

IV in which $R^1$, $R^2$, $R^3$, $R^4$ are n are as defined above; and 2. treating one mole of compound IV with at least one mole of cyanogen bromide, but preferably about 1.0 to 2.0 moles, and most preferably about 1.0 to 1.1 moles, in a reaction inert organic solvent, i.e., a (lower)alkanol, preferably ethanol, n-propanol, isopropanol, with or without the presence of some water, with the aid of heat, preferably at about reflux temperatures, to produce compound I.

The pharmaceutically acceptable, nontoxic salts of compound I are readily prepared by the addition of stoichiometric (or larger quantities) of the desired acid to a solution of compound I. Since compound I has only one strongly basic grouping, it only forms monosalts, e.g., monohydrochloride.

A preferred embodiment of the present invention is the compound having the formula

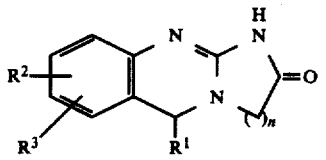

I in which $R^1$ is H, phenyl or (lower)alkyl, $R^2$ and $R^3$ when alike are hydrogen, chloro, bromo, fluoro, hydroxy, (lower)alkoxy of 1 to 3 carbon atoms or (lower-)alkyl of 1 to 3 carbon atoms, $R^2$ and $R^3$ when different are hydrogen, chloro, bromo, fluoro, $CF_3$, $SO_3H$, hydroxy, phenyl, amino, nitro, (lower)alkyl or (lower)alkoxy or when taken together $R^2$ and $R^3$ are methylenedioxy or the residue of a phenyl ring (—C=CH—CH=

CH—), and n is an integer of 1 or 2; or a pharmaceutically acceptable acid addition salt thereof.

A more preferred embodiment is the compound having the formula

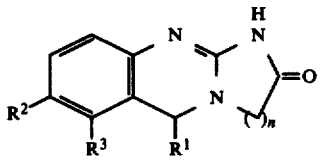

I in which $R^1$ is H, phenyl or (lower)alkyl, $R^2$ and $R^3$ when different are hydrogen, chloro, bromo, cluoro, $CF_3$, $SO_3H$, (lower)alkyl or (lower)alkoxy, hydroxy, nitro, amino, or phenyl, $R^2$ and $R^3$ when alike are hydrogen, chloro, bromo, fluoro, hydroxy, (lower)alkyl of 1 to 3 carbon atoms or (lower)alkoxy of 1 to 3 carbon atoms, or when taken together $R^2$ and $R^3$ are methylenedioxy or the residue of a phenyl ring (—CH=CH—CH=CH—), and n is an integer of 1 or 2; or a pharmaceutically acceptable acid addition salt thereof.

A more preferred embodiment is the compound having the formula

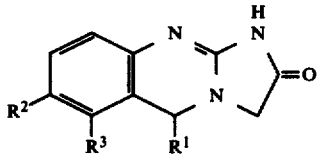

in which $R^1$ is H, phenyl or (lower)alkyl, $R^2$ and $R^3$ when different are hydrogen, chloro, bromo, fluoro, $CF_3$, $SO_3H$, hydroxy, (lower)alkyl or (lower)alkoxy, nitro, amino or phenyl, $R^2$ and $R^3$ when alike are hydrogen, chloro, bromo, fluoro, hydroxy, (lower)alkyl of 1 to 3 carbon atoms or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

A still more preferred embodiment is the compound having the formula

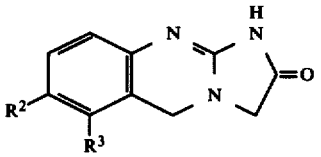

in which $R^2$ and $R^3$ when differnt are hydrogen, $CF_3$, $SO_3H$, chloro, bromo, fluoro, nitro, amino, hydroxy, (lower)alkoxy or (lower)alkyl, $R^2$ and $R^3$ when alike are hydrogen, chloro, bromo, fluoro, hydroxy, (lower)alkyl of 1 to 3 carbon atoms or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

A most preferred embodiment is the compound having the formula

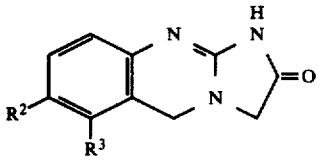

in which $R^2$ and $R^3$ are alike or different and are H, hydroxy, (lower)alkyl of 1 to 3 carbon atoms or (lower)alkoxy of 1 to 3 carbon atoms, chloro or fluoro; or a pharmaceutically acceptable salt thereof.

Another more preferred embodiment is the compound having the formula

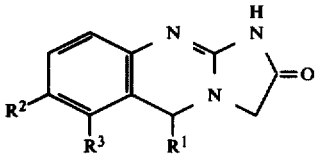

IM in which $R^2$ and $R^3$ are alike or different and are H, Cl, methoxy, methyl, nitro or hydroxy and $R^1$ is H, phenyl or methyl; or the hydrochloride salt thereof.

The most preferred embodiments are the compounds of formula IM in which

1. $R^1$, $R^2$ and $R^3$ are H;
2. $R^2$ and $R^3$ are methoxy and $R^1$ is H;
3. $R^1$ and $R^2$ are H and $R^3$ is methoxy;
4. $R^2$ is methoxy and $R^1$ and $R^3$ are H;
5. $R^1$ and $R^2$ are H and $R^3$ is methyl;
6. $R^2$ is methyl and $R^1$ and $R^3$ are H;
7. $R^2$ and $R^3$ are methyl and $R^1$ is H;
8. $R^2$ and $R^3$ taken together are —CH=CH—CH=CH— and $R^1$ is H;
9. $R^2$ is $NO_2$, $R^3$ is methyl and $R^1$ is H; or the hydrochloride salts thereof;
10. $R^2$ is chloro, $R^3$ is methyl and $R^1$ is H; or the hydrochloride salt thereof;
11. $R^1$ and $R^3$ are $CH_3$ and $R^2$ is H; or the hydrochloride salt thereof.

For the purpose of this disclosure, the term (lower)alkyl shall mean straight and branched chain saturated aliphatic groups having 1 to 6 carbons inclusive unless otherwise stated. The term (lower)alkanol or (lower)alkoxy shall have the same connotation, an alcohol or alkoxy group of 1 to 6 carbons inclusive unless otherwise stated.

Pharmacological evaluation has indicated the compounds of the present invention possess hypotensive activity.

The blood pressure of unanesthetized rats and dogs was measured directly by means of a transducer attached to an intra-arterial cannula and in anesthetized dogs by a mercury manometer attached to a carotid cannula.

The compounds of the instant invention were tested as the hydrochloride salts by the above method in genetically hypertensive rats in doses of 50 mg./kg. orally.

At the present time, indications are that the compounds do not appear to be acting in the same way as 2-(2,6-dichloroanilino)-2-imidazoline hydrochloride ["CATAPRES"]. Their activity is probably not attributable to α-adrenergic blockade or to ganglionic blocking action.

In the treatment of hypertension in animals including man, the compounds of the present invention are administered orally and/or parenterally, in accordance with conventional procedures for the administration of hypotensive agents in an amount of from about 0.5 mg./kg./dose to 30 mg./kg./dose depending upon the route of administration and the particular compound of the invention. The preferred dosage for the compounds of the invention is in the range of about 1.0 to 15.0 mg./kg./dose two to four times a day.

Pharmacological evaluation has also indicated the compounds of the present invention possess blood platelet anti-aggregative activity.

The aggregometer method of Born (1), as modified by Mustard et al. (2) was used to assess the in vitro activity of the various compounds as to inhibition of adenosine diphosphate (ADP) and collagen induced platelet aggregation. Platelet rich plasma was separated by centrifugation from citrated (3.8 percent) rabbit blood. ADP in final concentration of 0.5 mcg./ml. or 0.05 ml. of a collagen suspension prepared according to the method described by Evans et al. (3) was used to induce aggregation. The various compounds tested were dissolved in dimethylsulfoxide (DMSO) so that 5 mcl. added to the platelet rich plasma would yield the desired test concentration. Vehicle control trials were done and compared with aggregation induced in platelet rich plasma containing various concentrations of the test compounds. Dose response curves were obtained and Effective Concentration (EC50) values calculated.

1. Born, G. V. R., J. Physiol., London, 162, 67P (1962).
2. Mustard, J. F., Hegardt, B. Rowsell, H. C. and MacMillan, R. L., J. Lab. Clin. Med. 64, 548 (1964).
3. Evans, G. Marian M. C., Packham, M. A., Nishizawa, E. E., Mustard, J. F. and Murphy, E. A., J. Exp. Med., 128, 877 (1968).

Table I is illustrative of the hypotensive and blood platelet anti-aggregative activity of some of the preferred embodiments of the present invention.

TABLE I

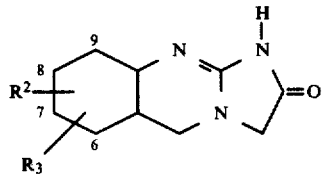

| Compound No. | R Position 6 | 7 | 8 | 9 | Blood Pressure % Change Rats P.O. 50 mg./kg. | In Vitro $EC_{50}$ (mcg/ml.) ADP | Collagen | In Vivo/In Vitro* Rabbits I.P. $ED_{50}$ (mg./kg.) ADP | Dogs P.O. 5 mg./kg. ADP % Inhibition |
|---|---|---|---|---|---|---|---|---|---|
| 1 | H | H | H | H | −36 ± 6 | 6 | 2 | >72 | |
| 2 | Cl | H | H | H | −37 ± 8 | 1 | 0.02 | 2 | |
| 3 | H | Cl | H | H | −4 ± 5 | 0.5 | 0.2 | >10 | |
| 4 | H | H | Cl | H | −14 | 6 | 1.5 | 18 | |
| 5 | H | H | H | Cl | −10 ± 1 | 7 | 0.3 | 6 | |
| 6 | H | Br | H | H | −8 ± 3 | 0.4 | 0.2 | 5 | |
| 7 | H | H | F | H | −27 ± 3 | 6 | 2 | >10 | |
| 8 | H | $NO_2$ | H | H | 5 ± 2 | 2 | 0.2 | >10 | |
| 9 | H | $NH_2$ | H | H | −10 ± 14 | 50 | 6 | | |
| 10 | $CH_3$ | H | H | H | −37 ± 8 | 0.5 | 0.1 | 0.6 | 76 |
| 11 | H | $CH_3$ | H | H | | 2 | 0.3 | >10 | |
| 45 | $CH_3$ | Cl | H | H | | 0.09 | 0.012 | — | 46 ± 8 |
| 12 | H | H | H | $CH_3$ | −22 ± 10 | 4 | 3 | >10 | |
| 13 | OME | H | H | H | −20 ± 14 | 0.5 | 0.2 | 4 | 19 |
| 14 | H | OME | H | H | −19 ± 4 | 1 | 0.2 | 4 | 17 |
| 15 | H | H | H | OME | −16 ± 3 | NA | NA | | |
| 16 | OME | OME | H | H | | 0.4 | | 0.7 | |
| 17 | H | OME | OME | H | +26 | 5 | | 4 | 0 |
| 18 | H | 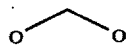 | | H | −25 ± 12 | 0.7 | 0.07 | >50 | |
| 39 | —CH=CH—CH=CH— | | H | H | −59 | — | — | — | — |

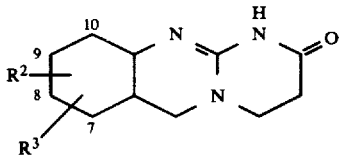

| | R Position 7 | 8 | 9 | 10 | | | | | |
|---|---|---|---|---|---|---|---|---|---|
| 19 | H | H | H | H | −32 ± 4 | 25 | 4 | | |
| 20 | Cl | H | H | H | −12 ± 1 | 6 | 0.7 | 8 | |
| 21 | H | Br | H | H | Toxic | 3 | 1.5 | 9 | |
| 22 | $CH_3$ | H | H | H | −26 ± 9 | 3 | 0.3 | >10 | |
| 23 | H | $CH_3$ | H | H | −7 ± 2 | 16 | 2 | | |

TABLE I-continued

| | | | | | | | | |
|---|---|---|---|---|---|---|---|---|
| 24 | H | H | H | $CH_3$ | −19 | NA | NA | |
| 25 | OME | H | H | H | 5 ± 3 | 2 | 0.4 | 8 |
| 26 | H | OME | H | H | 19 ± 6 | 6 | 1.5 | >10 |
| 27 | H | H | H | OME | −1 ± 4 | NA | NA | |
| 28 | H | OME | OME | H | −7 ± 2 | NA | 32 | |

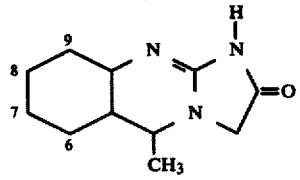

| | R Position | | | | | | | |
|---|---|---|---|---|---|---|---|---|
| | 6 | 7 | 8 | 9 | | | | |
| 29 | H | H | H | H | −28 | 2 | 7 | 35 |
| 50 | $CH_3$ | H | H | H | −49 | | | |
| 51 | H | $CH_3$ | H | H | −34 | | | |

+Denotes an increase in b.p.
−Denotes a decrease in b.p.

*In vivo/In vitro testing:

Before dosing the animals, blood samples are taken. The blood is centrifuged to obtain the blood platelet-rich plasma. Aggregation of this plasma is induced with ADP or collagen. This is the control.

The animals are then dosed with the compounds to be tested (orally or parenterally). Depending upon the route of administration, 1 to 2 hours are allowed to elapse after dosing. Blood is drawn and the same procedure employed as for the control in untreated animals.

The dose required to produce 50% inhibition of the aggregation is determined by dose response data obtained in this manner.

Experimental

All products described are supported by satisfactory infrared (IR) and nuclear magnetic resonance (nmr) spectra. Melting points are uncorrected. Temperatures are expressed in degrees Centigrade (°C.) and pressures in millimeters of mercury (mm).

EXAMPLE 1

Preparation of N-(o-Nitrobenzyl)ethyl glycine

To a suspension of 55.9 g. ($4.0\times10^{-1}$ moles) of ethyl glycine hydrochloride in 300 ml. of absolute ethyl alcohol was slowly added (~5 minutes) under a nitrogen atmosphere a solution of 70 ml. ($5.0\times10^{-1}$ moles) of triethylamine in 200 ml. of absolute ethyl alcohol. The mixture was heated to reflux and a solution of 17.2 g. ($1.0\times10^{-1}$ moles)o-nitrobenzylchloride in 200 ml. of absolute ethyl alcohol was added over a 1.5 hour period. Upon complete addition, the mixture was allowed to reflux for 18 hours, cooled to room temperature and the solvent removed in vacuo. To the solid residue was added 500 ml. of water and enough 10% hydrochloric acid to make the solution acidic (pH~3). The acidic solution was washed with methylene chloride (2×150 ml.), made neutral (pH~7) by the addition of saturated sodium bicarbonate and the insoluble oil extracted with methylene chloride (2×250 ml). The methylene chloride extracts were combined, washed with water (250 ml.), dried ($K_2CO_3$) and the solvent removed in vacuo resulting in a yellow oil. Owing to the instability of the oil toward distillation, the compound was used as such in subsequent reaction.

EXAMPLE 2

Preparation of N-(o-Aminobenzyl)ethyl glycine.

To a solution of 13.0 g. ($5.46\times10^{-2}$ moles) of N-(o-nitrobenzyl)ethyl glycine in 200 ml. of absolute ethyl alcohol was added slowly 0.76 g. (5% by weight) of 10% Pd/C catalyst and the mixture placed on a Paar hydrogenator. The mixture was shaken until theoretical hydrogen ($16.4\times10^{-2}$ moles) had been absorbed, removed from the Paar and the mixture filtered under suction. The catalyst was washed with ethyl alcohol and the solvent removed in vacuo affording a yellow oil. Purification of the oil was effected by distillation yielding 8.8 g. (77% yield) of a colorless oil; b.p. 124°-126° C. (0.03 mm).

Anal. calc'd. for $C_{11}H_{16}N_2O_2$:C, 63.44, H, 7.74, N, 13.45. Found: C, 63.57; H, 7.89; N, 13.57.

EXAMPLE 3

Preparation of 1,2,3,5-tetrahydroimidazo [2,1-b]-quinazolin-2-one (1).

To a solution of 6.24 g. ($3.0\times10^{-2}$ moles) of N-(o-aminobenzyl)ethyl glycinate in 150 ml. of 95% ethyl alcohol was poured at room temperature a solution of 3.19 g. ($3.0\times10^{-2}$ moles) of cyanogen bromide in 30 ml. of 95% ethyl alcohol. The mixture was allowed to stir at room temperature for 15 minutes, heated to reflux for 18 hours, cooled to room temperature and the solvent removed in vacuo. To the resulting semi-solid mass was added 200 ml. of water and it was made basic (pH 10) by the addition of a saturated sodium bicarbonate solution. After stirring for 0.5 hours at room temperature, the precipitate was filtered, washed with water and dried under high vacuum/$P_2O_5$ resulting in 3.33 g. (65% yield) of a colorless powder, mp. >285° C. Purification could be effected by crystallization from hot dimethylformamide or by formation of the hydrochloride salt from acetonitrile/ether solvent pair.

1,2,3,5-tetrahydroimidazo-[2,1-b]-quinazolin-2-one hydrochloride: mp. 259°-263° W/decomp.

Anal. calc'd. for $C_{10}H_9N_3O.HCl$: C, 53.70; H, 4.51; N, 18.79; Cl, 15.85. Found: C, 53.57; H, 4.79; N, 18.93; Cl, 15.77.

EXAMPLE 4

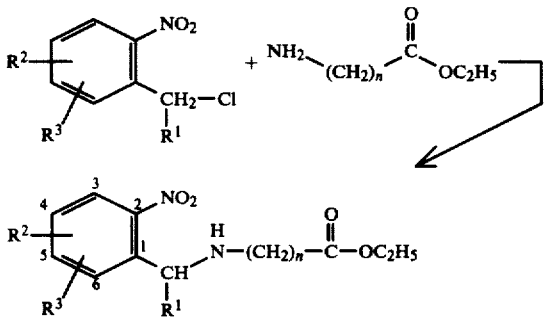

III

Preparation of Substituted N-(o-Nitrobenzyl)-Ethyl Glycinates. Glycinates

Substitution in the procedure of Example 1 for the o-nitrobenzyl chloride used therein of an equimolar quantity of the appropriately $R^1$, $R^2$, $R^3$-substituted o-nitrobenzylchloride produced the compounds having formula III in which n, $R^1$, $R^2$ and $R^3$ are as designated:

| Compound No. | $R^1$ | $R^2$ | $R^3$ | n |
|---|---|---|---|---|
| 2A | H | H | 6-Cl | 1 |
| 3A | H | H | 5-Cl | 1 |
| 4A | H | H | 4-Cl | 1 |
| 5A | H | H | 3-Cl | 1 |
| 7A | H | H | 4-F | 1 |
| 10A | H | H | 6-$CH_2$ | 1 |
| 11A | H | H | 5-$CH_2$ | 1 |
| 12A | H | H | 3-$CH_2$ | 1 |
| 13A | H | H | 6-$OCH_2$ | 1 |
| 14A | H | H | 5-$OCH_2$ | 1 |
| 15A | H | H | 3-$OCH_2$ | 1 |
| 16A | H | 5-$OCH_2$ | 6-$OCH_2$ | 1 |
| 17A | H | 4-$OCH_2$ | 5-$OCH_2$ | 1 |

-continued

| Compound No. | $R^1$ | $R^2$ | $R^3$ | n |
|---|---|---|---|---|
| 18A | H | $R^2$ and $R^3$ are methylenedioxy | | 1 |
| 19A | H | H | H | 2 |
| 20A | H | H | 6-Cl | 2 |
| 22A | H | H | 6-$CH_2$ | 2 |
| 23A | H | H | 5-$CH_3$ | 2 |
| 24A | H | H | 3-$CH_3$ | 2 |
| 25A | H | H | 6-$OCH_3$ | 2 |
| 26A | H | H | 5-$OCH_3$ | 2 |
| 27AA | H | H | 3-$OCH_2$ | 2 |
| 28A | H | 4-$OCH_3$ | 5-$OCH_2$ | 2 |
| 29A | $CH_2$ | H | H | 1 |
| 30A | $CH_2$ | H | H | 2 |
| 31A | H | 3-$CH_2$ | 6-$CH_3$ | 1 |
| 32A | H | H | 6-Br | 1 |
| 33A | H | H | 6-F | 1 |

EXAMPLE 5

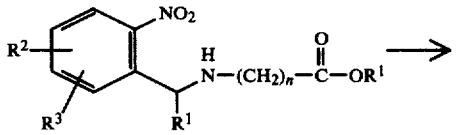

III

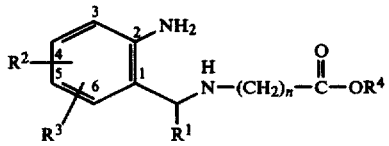

IV

Substitution in the procedure of example 2 for the N-(o-nitrobenzyl)ethylglycine used therein of an equimolar quantity of the appropriately $R^1$, $R^2$, $R^3$-substituted compound III produced the compounds having the formula IV:

| Compound No. | n | $R^1$ | $R^2$ | $R^3$ | $R^4$ | b.p.(mm.) | G yield |
|---|---|---|---|---|---|---|---|
| 2B | 1 | H | H | 6-Cl | Et | **m.p. 185–186° C. as 2 HCl | *80 G crude |
| 3B | 1 | H | H | 5-Cl | Et | ** | * |
| 4B | 1 | H | H | 4-Cl | Et | ** | * |
| 5B | 1 | H | H | 3-Cl | Et | ** | * |
| 7B | 1 | H | H | 4-F | Et | 138° C. (0.35) | *63 (crude) |
| 10B | 1 | H | H | 6-$CH_3$ | Et | 170° C. (0.3) | |
| 11B | 1 | H | H | 5-$CH_3$ | Et | 129–133° C. (0.1) | |
| 13B | 1 | H | H | 6-$OCH_3$ | Et | ** | |
| 14B | 1 | H | H | 5-$OCH_3$ | Et | 162–164° C. (0.3) | 98 (crude) |
| 15B | 1 | H | H | 3-$OCH_3$ | Et | ** | |
| 16B | 1 | H | 5-$OCH_3$ | 5-$OCH_3$ | Et | ** | |
| 17B | 1 | H | 4-$OCH_3$ | 6-$OCH_3$ | Et | *m.p. 202–203° C. | 93 (crude) |
| 18B | 1 | H | $R^2$ and $R^3$ are methylenedioxy | | Et | ** | 99 (crude) |
| 19B | 2 | H | H | H | Et | m.p. 178–180° C. as HCl | 52 |
| 20B | 2 | H | H | 6-Cl | Et | m.p. 191–193° C. as 2.HCl | * |
| 22B | 2 | H | H | 6-$CH_3$ | Et | m.p. 204– | |

-continued

| Compound No. | n | $R^1$ | $R^2$ | $R^3$ | $R^4$ | b.p.(mm.) | G yield |
|---|---|---|---|---|---|---|---|
| | | | | | | 206° C. as 2.HCl | |
| 23B | 2 | H | H | 5-$CH_3$ | Me | 126–129° C. (0.06) | |
| 24B | 2 | H | H | 3-$CH_3$ | Me | 136° C. (0.07) | |
| 25B | 2 | H | H | 6-$OCH_3$ | Me | ** | |
| 26B | 2 | H | H | 5-$OCH_3$ | Me | ** | |
| 27B | 2 | H | H | 3-$OCH_3$ | Me | ** | |
| 28B | 2 | H | 4-$OCH_3$ | 5-$OCH_3$ | Me | ** | |
| 29B | 1 | $CH_3$ | H | H | Et | ** | |
| 30B | 2 | $CH_3$ | H | H | Me | ** | |
| 31B | 1 | H | 3-$CH_3$ | 6-$CH_3$ | Et | ** | 92 |
| 32B | 1 | H | H | 6-F | Et | ** | 74 |
| 33B | 1 | H | H | 4-$CH_3$ | Et | M P 182–3° C. | 78 |
| 34B | 1 | H | H | 4-$CH_3$ | Et | ** | 97 |
| 35B | 1 | H | 4-$CH_3$ | 6-$CH_3$ | Et | ** | 88 |
| 36B | 1 | H | 4-$CH_3$ | 5-$CH_3$ | Et | ** | 91 |
| 37B | 1 | H | 5-$CH_3$ | 6-$CH_3$ | Et | ** | 99 |
| 38B | 1 | H | H | 6-Et | Et | ** | 90 |
| 39B | 1 | H | 5.6-CH=CH—CH=CH— | | Et | ** | 92 |
| 40B | 1 | H | 4-Cl | 6-Cl | Et | ** | 92 Example 19 |
| 41B | 1 | H | 3-Cl | 6-Cl | Et | ** | Example 21 |
| 42B | 1 | H | H | 6-Br | Et | ** | 74 Example 18 |
| 43B | 1 | H | H | 6-$CF_3$ | Et | ** | Example 20 |

*These reductions were carried out in the presence of two equivalents of hydrochloric acid
**Compounds could not be distilled used crude in subsequent reactions

EXAMPLE 6

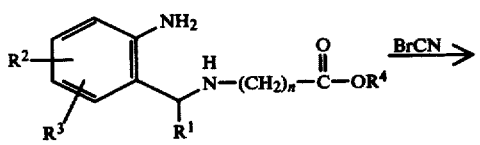

IV

-continued

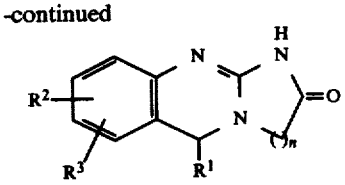

I

Substitution in the procedure of example 3 for the N-(o-aminobenzyl)ethyl glycinate used therein of an equimolar quantity of the appropriate compound IV described in example 5 produced the compounds I listed below:

| Compound No. | n | $R^1$ | $R^2$ | $R^3$ | m.p. (HCl)C.° |
|---|---|---|---|---|---|
| 2 | 1 | H | H | 6-Cl | 245° w/decomp. |
| 3 | 1 | H | H | 7-Cl | >250°* |
| 4 | 1 | H | H | 8-Cl | 251–53° w/decomp. |
| 5 | 1 | H | H | 9-Cl | 261–64° w/decomp. |
| 7 | 1 | H | H | 8-F | 280° w/decomp. |
| 10 | 1 | H | H | 6-$CH_3$ | >250° |
| 11 | 1 | H | H | 7-$CH_3$ | 265–70° C. |
| 12 | 1 | H | H | 9-$CH_3$ | >280° |
| 13 | 1 | H | H | 6-$OCH_3$ | 288–290° |
| 14 | 1 | H | H | 7-$OCH_3$ | 267–70° w/decomp. |
| 15 | 1 | H | H | 9-$OCH_3$ | 262–264° |
| 16 | 1 | H | 6-$OCH_3$ | 7-$OCH_3$ | 263–65°* |
| 17 | 1 | H | 8-$OCH_3$ | 7-$OCH_3$ | 227–28 w/decomp.* |
| 18 | 1 | H | | $R^2$ and $R^3$ are 7,8-methylene-dioxy | >250°* |
| 19 | 2 | H | H | H | 260–64°* |
| 20 | 2 | H | H | 7-Cl | >280°* |
| 22 | 2 | H | H | 7-$CH_3$ | >280°* |
| 23 | 2 | H | H | 8-$CH_3$ | 269–72° (free base)* |
| 24 | 2 | H | H | 10-$CH_3$ | 192–95° (free base)* |
| 25 | 2 | H | H | 7-$OCH_3$ | 274–81° decomp.* |
| 26 | 2 | H | H | 8-$OCH_3$ | 254–56°* |
| 27 | 2 | H | H | 10-$OCH_3$ | 272–74°* |
| 28 | 2 | H | 9-$OCH_3$ | 8-$OCH_3$ | 269–73°* |

-continued

| Compound No. | n | $R^1$ | $R^2$ | $R^3$ | m.p. (HCl)C.° |
|---|---|---|---|---|---|
| 29 | 1 | $CH_3$ | H | H | 266–67°* |
| 30 | 2 | $CH_3$ | H | H | >275°* |
| 31 | 1 | H | 9-$CH_3$ | 6-$CH_3$ | >200° decomp. |
| 32 | 1 | H | H | 6-F | 275–280° decomp. |
| 33 | 1 | H | H | 8-$CF_3$ | >275° |
| 34 | 1 | H | H | 8-$CH_3$ | >200° decomp. |
| 35 | 1 | H | 8-$CH_3$ | 6-$CH_3$ | >200° decomp. |
| 36 | 1 | H | 8-$CH_3$ | 7-$CH_3$ | >200° decomp. |
| 37 | 1 | H | 7-$CH_3$ | 6-$CH_3$ | >200° decomp. |
| 38 | 1 | H | H | 6-Et | >200° decomp. |
| 39 | 1 | H | 6.7-CH=CH—CH=CH— | | >275° C. |
| 40 | 1 | H | 8-Cl | 6-Cl | >275° C. |
| 41 | 1 | H | 9-Cl | 6-Cl | >275° C. |
| 42 | 1 | H | H | 6-Br | >275° C. |
| 43 | 1 | H | H | 6-$CF_3$ | 302° C. decomp. |

| Compound No. | Analyses |
|---|---|
| 2. | Anal. calc'd. for $C_{10}H_3ClN_2O.HCl$: C, 46.53; H, 3.51; N, 16.28; Cl, 27.47. Found: C, 46.60; H, 3.68; N, 16.14; Cl, 27.32. |
| 3. | Anal. calc'd. for $C_{10}H_2ClN_2O$: C, 54.19; H, 3.64; N, 18.96; Cl, 16.00. Found: C, 54.35; H, 3.73; N, 19.19; Cl, 15.87. |
| 4. | Anal. calc'd. for $C_{10}H_3ClN_2O.HCl_2H_2O$: C, 44.96; H, 3.77; N, 15.73; Cl, 26.54. Found: C, 45.07; H, 3.99; N, 15.82, Cl, 25.90. |
| 5. | Anal. calc'd. for $C_{10}H_2ClN_2O$; C, 54.19; H, 3.64; N, 18.96; Cl, 16.00. Found: C, 54.35; H, 3.87; N, 19.22; Cl, 16.18. |
| 7. | Anal. calc'd for $C_{10}H_3FN_1O$ HCl C, 4970; H, 3.75; N, 17.14. Found: C, 50.07; H, 3.86; N, 17.96. |
| 10. | Anal. calc'd. for $C_{11}H_{11}N_2O$ HCl $\frac{1}{2}H_2O$ C, 52.41; H, 5.25; N, 16.83; Cl, 14.20 C, 53.20; H, 5.28; N, 17.00; Cl, 14.28; |
| 11. | Anal. calc'd. for $C_{11}H_{11}N_2O$ HCl $H_2O$ C, 51.66; H, 5.52; N, 16.43; Cl, 13.86 Found: C, 52.07. H, 5.74; N, 16.57; Cl, 13.96 |
| 12. | Anal. calc'd. for $C_{11}H_{11}N_2O$ HCl C, 55.59; H, 5.09; N, 17.68; Found: C, 55.59. H, 5.25; N, 17.87 |
| 13. | Anal. calc'd. for $C_{11}H_{11}N_2O_2HCl$ C, 52.08; H, 4.77; N, 16.56. Found: C, 51.54, H, 4.84; N, 16.69. |
| 14. | Anal. calc'd. for $C_{11}H_{11}N_2O_2HCl$ C, 52.08; H, 4.77; N, 16.56; Cl, 13.98; Found: C, 51.82, H, 4.92; N, 16.70; Cl, 14.22. |
| 15. | Anal. calc'd. for $C_{11}H_{11}N_2O_2HCl$ $\frac{1}{2}H_2O$; C, 50.29; H, 4.99; N, 15.99 Found: C, 50.60; H, 4.99; N, 16.07. |
| 16. | Anal. calc'd. for $C_{12}H_{12}N_2O_3HCl$ C, 50.80; H, 4.97; N, 14.81; Found: C, 50.64; H, 5.12; N, 14.51. |
| 17. | Anal. calc'd. for $C_{12}H_{12}N_2O_3HCl.\frac{1}{2}H_2O$; C, 49.23; H, 5.17; N, 14.36; Cl, 12.11 Found: C, 49.46; H, 4.92; N, 14.48; Cl, 12.28. |
| 18. | Anal. calc'd. for $C_{11}H_1N_3O_2$ C, 57.14; H, 3.92; N, 18.17. Found: C, 57.13; H, 4.01; N, 18.48. |
| 19. | Anal. calc'd. for $C_{11}H_{11}N_2O$; C, 65.67; H, 5.51; N, 20.88. |

-continued

| Compound No. | Analyses |
|---|---|
| | Found: C, 65.61; H, 5.62; N, 20.70. |
| 20. | Anal. calc'd. for $C_{11}H_{10}ClN_2O.HCl$ C, 48.55; H, 4.08; N, 15.44 Found: C, 48.28; H, 4.37; N, 15.21. |
| 22. | Anal. calc'd. for $C_{10}H_{10}N_2O.HCl$: C, 57.26; H, 5.61; N, 16.69; Cl, 14.08 Found: C, 56.96; H, 5.66; N, 16.90; Cl, 14.15. |
| 23. | Anal. calc'd. for $C_{10}H_{13}N_2O$: C, 66.95; H, 6.09; N, 19.52. FOund: C, 64.09; H, 6.35; N, 19.40. |
| 24. | Anal. calc'd. for $C_{12}H_{13}N_2O$: C, 66.95; H, 6.09; N, 19.52. Found: C, 66.87; H, 6.34; N, 19.85. |
| 25. | Anal. calc'd. for $C_{12}H_{13}N_2O_2\frac{1}{2}H_2O$: C, 60.01; H, 5.46; N, 17.49. Found: C, 60.12; H, 5.74; N, 17.54. |
| 26. | Anal. calc'd. for $C_{12}H_{12}N_2O_2.HCl$: C, 53.84; H, 5.27; N, 15.70. Found: C, 53.77; H, 5.47; N, 15.45. |
| 27. | Anal. calc'd. for $C_{12}H_{12}N_2O_2.HCl$ $\frac{1}{2}H_2O$: C, 52.08; H, 5.46; N, 15.19. Found: C, 51.78; H, 5.13; N, 15.08. |
| 28. | Anal. calc'd. for $C_{12}H_{15}N_2O_3$ $\frac{1}{2}H_2O$: C, 57.77; H, 5.97; N, 15.55. Found: C, 57.42; H, 6.02; N, 15.36. |
| 29. | Anal. calc'd. for $C_{11}H_{11}N_2O$: C, 65.66 H, 5.51; H, 20.88. Found: C, 65.40; H,: 5.56; N, 20.51. |
| 30. | Anal. calc'd. for $C_{10}H_{12}N_2O$: C, 66.96; H, 6.09; N, 19.52. Found: C, 67.07; H, 6.36; N, 19.34. |
| 31. | Anal. calc'd. for $C_{12}H_{13}N_2O.HCl$: C, 57.26; H, 5.61; N, 16.69; Cl, 14.08. Found: C, 57.43; H, 5.85; N, 16.70; Cl, 13.75. |
| 32. | Anal. calc'd. for $C_{10}H_2FN_2O.HCl$: C, 49.70; H, 3.75; N, 17.39. Found: C, 49.55; H, 3.98; N, 17.42. Anal. calc'd. for $C_{11}H_3F_3N_3O$: C, 51.77; H, 3.16; N, 16.47. Found: C, 51.70; H, 3.19; N, 16.23. |
| 34. | Anal. calc'd. for $C_{11}H_{11}N_3O$: C, 65.67; H, 5.51; N, 20.88. Found: C, 64.79; H, 5.70; N, 20.82. |

-continued

| Compound No. | Analyses |
|---|---|
| 35. | Anal. calc'd. for $C_{12}H_{12}N_2O.HCl.H_2O$: C, 53.44; H, 5.98; N, 15.58; Cl, 13.14. Found: C, 53.71; H, 6.13; N, 15.6; Cl, 12.84. |
| 36. | Anal. calc'd. for $C_{12}H_{13}N_3O.HCl.H_2O$: C, 53.64; H, 5.63; N, 15.64; Cl, 13.19. Found: C, 53.91; H, 5.92; N, 15.75; Cl, 13.36. |
| 37. | Anal. calc'd. for $C_{12}H_{13}N_3O$: C, 66.95; H, 6.09; N, 19.52. Found: C, 66.83; H, 6.23; N, 19.30. |
| 38. | Anal. calc'd. for $C_{12}H_{13}N_2O.HCl$: C, 57.26; H, 5.61; N, 16.69; Cl, 14.08. Found: C, 56.93; H, 5.61; N, 16.81; Cl, 14.02. |
| 39. | Anal. calc'd. for $C_{14}H_{11}N_3O.HCl$: C, 61.43; H, 4.42; N, 15.35. Found: C, 61.52; H, 4.96; N, 12.17. |
| 40. | Anal. calc'd. for $C_{10}H_7Cl_2N_3O$: C, 46.90; H, 2.76; N, 16.41. Found: C, 46.90; H, 2.91; N, 16.38. |
| 41. | Anal. calc'd. for $C_{10}H_7Cl_2N_3O$: C, 46.90; H, 2.76; N, 16.41. Found: C, 46.64; H, 3.00; N, 16.39. |
| 42. | Anal. calc'd. for $C_{10}H_2BrN_2O.HCl$: C, 39.69; H, 3.00; N, 13.89. Found: C, 39.62; H, 3.17; N, 14.02. |
| 43. | Anal. calc'd. for $C_{11}H_2F_3N_3O$: C, 51.77; H, 3.16; N, 16.47. Found: C, 51.50; H, 3.41; N, 16.52. |

The IR (infrared) and NMR (nuclear magnetic resonance) spectra of all the compounds were consistent with the structure.

EXAMPLE 7

Ethyl β-(o-Nitrobenzylamino)-propionate (see J.A.C.S., 80, 1168 (1958)

o-Nitrobenzylamine hydrochloride (20.4 g., 0.114 mole) was dissolved in a minimum volume of water and the solution was made strongly basic by addition of 10% sodium hydroxide. The clear oil which formed was extracted into two 120-ml. portions of ether. The ether was dried with 10 g. of anhydrous sodium sulfate, filtered, and finally dried over Drierite. The dried solution was filtered and evaporated, leaving a yellow oil. The oil was dissolved in 100 ml. of absolute ethanol and 11.4 g (0.114 mole) of freshly distilled ethyl acrylate was added. This solution was allowed to stand overnight and the solvent removed by distillation from a steam-cone. The oily residue was dissolved in 200 ml. of dry ether, the solution was cooled in an ice bath, and treated with dry hydrogen chloride. When precipitation was complete, the solid was filtered and dissolved in 120 ml. of boiling absolute ethanol. The hydrochloride crystallized from this solution on cooling yielding 20.7 g. of the aminopropionate hydrochloride, m.p. 137.5°–139.0°. By concentrating and cooling the mother liquor, an additional 5 g. was obtained, m.p. 136.5°–138.5°, and by repeating this operation 1.1 g., m.p. 136°–139°, was obtained, raising the total yield to 26.8 g. (81.4%). The analytical sample was prepared by repeated crystallization from absolute ethanol to give a melting point of 138.5°–139.0°.

Anal. calc'd. for $C_{12}H_{17}O_4N_2Cl$: C, 49.91; H, 5.94; N, 9.70. Found: C, 49.9; H, 5.94; N, 9.51.

EXAMPLE 8

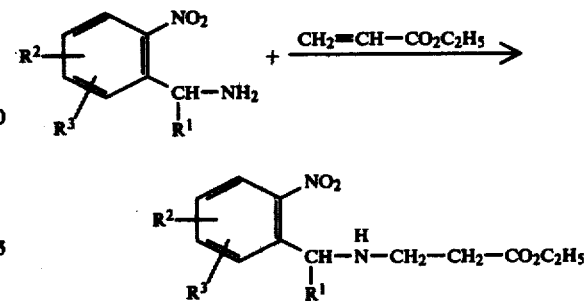

Substitution in the procedure of example 4 for the o-nitrobenzylamine used therein of an equimolar quantity of the appropriately $R^1$, $R^2$, $R^3$ substituted o-nitrobenzylamine produces compounds III in which $R^1$, $R^2$, $R^3$ - is as defined in the specification.

EXAMPLE 9

Preparation of 7-Bromo-1,2,3,5-tetrahydroimidazo[2,1-b]-quinazolin-2-one

To a vigorously stirred solution of 1.87 g. (0.01 mole) of 1,2,3,5-tetrahydroimidazo[2,1-b]-quinazolin-2-one in 40 ml. of glacial acetic acid was added dropwise at room temperature 1.60 g. (0.01 mole) of bromine. The mixture was stirred at room temperature for one hour, water (50 ml.) was added and the volume concentrated (10–15 ml.) in vacuo. Additional water (50 ml.) was added, the solution made basic with ammonium hydroxide, warmed and the insoluble material filtered under suction. The colorless solid was washed with water, dried and crystallized from 50 ml. of 5% hydrochloric acid yielding 0.8 g. (30% yield) of a colorless solid: m.p. >275°. Purification was effected by crystallization from methanol/ether; m.p. 275° to yield the title product.

Anal. calc'd. for $C_{10}H_8BrN_3O.HCl$: C, 39.70; H, 3.00; N, 13.89.

Found: C, 39.34; H, 3.20; N, 13.88.

EXAMPLE 10

Preparation of 7-Nitro-1,2,3,5-tetrahydroimidazo-[2,1-b]quinazolin-2-one

To a stirred, 0° suspension of 11.20 g. ($6.0\times10^{-2}$ moles) of 1,2,3,5-tetrahydroimidazo[2,1-b]-quinazolin-2-one in acetonitrile (150 ml.) was added dropwise 83.0 g. ($6.6\times10^{12}$ moles of nitric acid) of a 5% nitric acid/-sulfuric acid solution. The mixture was allowed to stir at 0° for 45 minutes, warmed to room temperature and stirred an additional 2 hours. The mixture was poured into 700 ml. of ice water, the organic layer separated, the acidic aquo solution washed with methylene chloride (2×100 ml.) and filtered. The aqueous solution was made basic (pH 8) by the dropwise addition of 40% sodium hydroxide, the basic solution stirred for 30 minutes and the precipitate filtered under suction. The yellow solid was washed with water, then acetone and dried under high vacuum (almost quantitative yield). The solid was suspended in water (350 ml.), the solution saturated with hydrogen chloride, heated to boiling and filtered. Saturated sodium chloride solution (100 ml.) was added, the mixture cooled and the precipitate isolated yielding 6.92 g. (43% yield) of a yellow powder. M.p. >280°: Spectral data was consistent with assigned structure: the 7-Nitro-1,2,3,5-tetrahydroimidazo[2,1-b]quinazolin-2-one-hydrochloride was used as such in subsequent reaction.

EXAMPLE 11

Preparation of 7-Amino-1,2,3,5-tetrahydroimidazo-[2,1-b]quinazolin-2-one

To a suspension of 9.18 g. ($3.4\times10^{-2}$ mole) of 7-Nitro-1,2,3,5-tetrahydroimidazo[2,1-b]-quinazolin-2-one hydrochloride in 95% ethanol (300 ml.) was added 10 ml. of concentrated hydrochloric acid and 0.45 g. of 10% Pd/C catalyst. The mixture was placed on a Paar hydrogenator, shaken until theoretical hydrogen absorbed, removed and water (150 ml.) added to effect dissolution of precipitate. The mixture was filtered under suction, the catalyst washed with 95% ethanol and the mixture evaporated to dryness yielding 9.02 g. of a yellow powder. Purification of the free base was effected yielding 7-Amino-1,2,3,5-tetrahydroimidazo[2,1-b]quinazolin-2-one; m.p. >275°.

Anal. calc'd. for $C_{10}H_{10}N_4O$: C, 59.39; H, 4.98; N, 27.71. Found: C, 59.14; H, 5.16; N, 28.03.

EXAMPLE 12

Preparation of 6-Hydroxy-1,2,3,5-tetrahydroimidazo[2,1-b]quinazolin-2-one

A mixture of 16.0 g. ($6.91\times10^{-2}$ moles) of compound 13 and 750 ml. of 48% aqueous hydrobromic acid was heated to reflux for 22 hours, the mixture cooled by the addition of ice, the precipitate filtered under suction, washed with water and dried. The precipitate was dissolved in a minimum amount of 1N hydrochloric acid, treated with charcoal, filtered and cooled (4°) overnight. The precipitate was isolated and dried yielding 4.65 g. of colorless needles; m.p. >280° to yield the title compound.

Anal. calc'D. for $C_{10}H_9O_2$.HCl: C, 50.11; H, 4.21; N, 17.53. Found: C, 49.82; H, 4.30; N, 17.33.

EXAMPLE 13

Preparation of 7-Hydroxy-1,2,3,5-tetrahydroimidazo[2,1-b]quinazolin-2-one

Substitution in the procedure of example 12 for the 6-methoxy-1,2,3,5-tetrahydroimidazo-[2,1-b]quinazolin-2-one-used therein of an equimolar quantity of 7-methoxy-1,2,3,5-tetrahydroimidazo[2,1-b]quinazolin-2-one produced the title product; m.p. 300° C.

Anal. calc'd. for $C_{10}H_9N_3O_2$.HCl: C, 50.11; H, 4.21; N, 17.53. Found: C, 50.31; H, 4.46; N, 17.42.

EXAMPLE 14

Preparation of 8-Bromo-6-[H]-1,2,3,4-tetrahydropyrimido[2,1-b]quinazolin-2-one Substitution in the procedure of example 9 for the 1,2,3,5-tetrahydroimidazo[2,1-b]-quinazolin-2-one used therein of an equimolar quantity of 6-[H]-1,2,3,4-Tetrahydropyrimido[2,1-b]-quinazolin-2-one at about 60° C. produced the title compound, m.p. 267°-269° C. w/decomp.

Anal. calc'd. for $C_{11}H_{10}BrN_3O$ $1/3H_2O$: C, 46.18; H, 3.76; N, 14.69. Found: C, 46.23; H, 3.63; N, 14.96.

EXAMPLE 15

Preparation of 6-Methyl-7-nitro-1,2,3,5-tetrahydroimidazo[2,1-b]quinazolin-2-one Substitution in the procedure of example 10 for the 1,2,3,5-tetrahydroimidazo[2,1-b]quinazolin-2-one used therein by an equimolar quantity of 6-methyl-1,2,3,5-tetrahydroimidazo[2,1-b]-quinazolin-2-one produced the title compound; m.p. >300°.

Anal. calc'd. for $C_{11}H_{10}N_4O_3$.HCl: C, 46.75; H, 3.92; N, 19.82; Cl, 12.54. Found: C, 46.95; H, 4.10; N, 19.66; Cl, 12.63.

EXAMMPLE 16

Preparation of N-(2,3-dimethyl-6-nitrobenzyl)ethyl glycinate

To a mixture of 1.80 g (10 mmole) of 2,3-dimethyl-6-nitrobenzyl amine, 0.60 g (5.6 mmole) of sodium carbonate in 30 ml of dimethylformamide heated to 80° was added dropwise over a 45 min period a solution of 1.25 ml (11 mmole) of ethyl bromoacetate in 10 ml of dimethylformamide. The mixture was allowed to stir at 80° for 16 hr., cooled, 15 ml of water added and the solvent removed in vacuo. The residue was diluted with water, acidified with 10% hydrochloric acid and the acidic solution washed with ether. The acidic aqueous solution was made basic with ammonium hydroxide, extracted with ether, the ethereal extracts combined, washed with water and dried ($Na_2SO_4$). Removal of the solvent in vacuo afforded 2.50 g (93% yield) of a brown solid. Purification was effected by crystallization from methylcyclohexane; m.p. 50°-3°.

Anal. calc'd. for $C_{13}H_{18}N_2O_4$: C, 58.64; H, 6.81; N, 10.52. Found: C, 58.77; H, 7.10; N, 10.40.

EXAMPLE 17

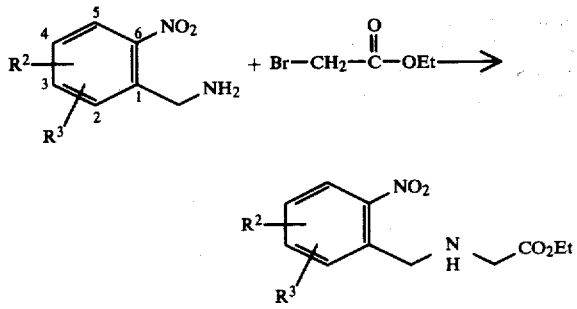

III

Substitution in the procedure of example 16 for the 2,3-dimethyl-6-nitrobenzylamine used therein of an equimolar quantity of the appropriately $R^2$, $R^3$-substituted o-nitrobenzylamine produced the compounds having formula III in which n, $R^2$ and $R^3$ are as designated:

| Compound No. | $R^2$ | $R^3$ | n | % Yield | mp (Hcl) |
|---|---|---|---|---|---|
| 33A | H | 4-$CF_3$ | 1 | 60 | 146-8 |

-continued

| Compound No. | $R^2$ | $R^3$ | n | % Yield | mp (Hcl) |
|---|---|---|---|---|---|
| 34A | H | 4-$CH_3$ | 1 | 77 | 122–4 |
| 35A | 4-$CH_3$ | 6-$CH_3$ | 1 | 79 | 136–7 |
| 36A | 4-$CH_3$ | 5-$CH_3$ | 1 | 47 | — |
| 37A | 5-$CH_3$ | 6-$CH_3$ | 1 | 41 | 50–3* |
| 38A | H | 6-Et | 1 | 45 | 154–7 |
| 39A | 2,3-CH=CH—CH=CH— | | 1 | 72 | — |
| 40A | 4-Cl | 6-Cl | 1 | 65 | oil |

33A: Anal. Calc'd. for $C_{12}H_{12}F_3N_2O_4$.HCl: C, 42.05; H, 4.12; N, 8.17. Found: C, 42.21;

34A: Anal. Calc'd. for $C_{12}H_{16}N_2O_4$.HCl: C, 49.99; H, 5.94; N, 9.70; Cl, 12.28. Found: C, 49.77; H, 6.03; N, 9.77; Cl, 12.58.

35A: Anal. Calc'd. for $C_{12}H_{18}N_2O_4$HCl:C, 51.57; H, 6.23; N, 9.26; Cl, 11.71. Found: C, 51.54; H, 6.39; N, 9.24; Cl, 11.59.

37A: Anal. Calc'd. for $C_{12}H_{18}N_2O_4$C, 58.64; H, 6.81; N, 10.52. Found: C, 58.77; H, 7.10; N, 10.40.

38A: Anal. Calc'd. for $C_{12}H_{18}N_2O_4$.HCl: C, 51.57; H, 6.32; N, 9.26; Cl, 11.71. Found: C, 51.39; H, 6.32; N, 9.49; Cl, 11.64.

EXAMPLE 18

Preparation of N-(2-amino-6-bromobenzyl)ethyl glycinate

To a stirred 0° solution of 113 g (0.50 moles) of stannous chloride-dihydrate in concentrated hydrochloric acid (125 ml) was added a solution of 31.69 g (0.10 moles) of N-(2-nitro-6-bromobenzyl)-ethyl glycine in concentrated hydrochloric acid (100 ml). After the initial rise in temperature subsided, the ice bath was removed, the mixture stirred for 0.5 hrs. and then warmed (45°–50°) on a steam bath for 1.5 hrs. The mixture was cooled to room temperature, poured into 1 liter of cooled 3.8 M sodium hydroxide, the mixture was rendered alkaline (pH 10) by the addition of 1N sodium hydroxide and extracted with ether. The etheral extracts were combined, washed with water, dried ($K_2CO_3$) and the solvent removed in vacuo affording 21.2 g (74% yield) of an orange oil which solidified on standing; mp 39°–41°.

Anal. Calc'd. for $C_{11}H_{15}BrN_2O_2$: C, 46.00; H, 5.27; N, 9.76. Found: C, 46.21; H, 5.33; N, 10.03.

EXAMPLE 19

Preparation of N-(2-amino-4,6-dichlorobenzyl)ethyl glycinate (40B)

Substitution in the procedure of example 18 for the N-(2-nitro-6-bromobenzyl)ethyl glycine used therein of an equimolar quantity of N-(2-nitro-4,6-dichlorobenzyl-)ethyl glycine produced the title product in 92% yield; m.p. 69.5°–70° C.

Anal. Calc'd. for $C_{11}H_{14}Cl_2N_2O_2$: C, 47.67; H, 5.09; N, 10.11. Found: C, 47.73; H, 5.33; N, 10.16.

EXAMPLE 20

Preparation of N-(2-amino-6-trifluoromethylbenzyl)-ethyl glycinate

To a suspension of 7.40 g (53 mmole) of ethyl glycine hydrochloride salt in 100 ml of methylene chloride was added under a nitrogen atmosphere 5.30 g (53 mmole) of triethylamine. To the stirred mixture was added portionwise 3.25 g (13 mmole) of 2-amino-6-trifluoromethylbenzyl chloride hydrochloride and upon complete addition, the mixture was stirred an additional 2 hrs at room temperature. The methylene chloride was removed in vacuo, water added to the residue and the mixture made basic with sodium bicarbonate. The mixture was extracted with ether, the ether extracts combined, washed with water and dried ($Na_2SO_4$). Removal of the solvent in vacuo afforded 3.68 g (99% yield) of a pale yellow oil. The sample was used as such without further purification.

EXAMPLE 21

Preparation of N-(2-amino-3,6-dichlorobenzyl)ethyl glycinate (41B)

Substitution in the procedure of example 20 for the 2-amino-6-trifluoromethylbenzyl chloride hydrochloride used therein of an equimolar quantity of 2-amino-3,6-dichlorobenzyl chloride hydrochloride produced the title product.

EXAMPLE 22

Preparation of 7-Bromo-6-methyl-1,2,3,5-tetrahydroimidazo[2,1-b]quinazolin-2-one (44)

Substitution in the procedure of example 9 for the 1,2,3,5-tetrahydroimidazo[2,1-b]quinazolin-2-one used therein of an equimolar quantity of 6-methyl-1,2,3,5-tetrahydroimidazo[2,1-b]quinazolin-2-one produced the title product.

Anal. calc'd. for $C_{11}H_{10}BrN_3O$: C, 47.16; H, 3.60; N, 15.00. Found: C, 46.87; H, 3.82; N, 15.26.

EXAMPLE 23

Preparation of 7-Chloro-6-methyl-1,2,3,5-tetrahydroimidazo[2,1-b]quinazolin-2-one (45)

Substitution in the procedure of example 9 for the 1,2,3,5-tetrahydroimidazo[2,1-b]quinazolin-2-one and bromine used therein of equimolar quantities of 6-methyl-1,2,3,5-tetrahydroimidazo[2,1-b]quinazolin-2-one and chlorine produced the title product.

Anal. calc'd. for $C_{11}H_{10}ClN_3O$.HCl: C, 48.55; H, 4.08; N, 15.44; Cl, 26.05. Found: C, 48.92; H, 4.45; N, 15.64; Cl, 22.38.

EXAMPLE 24

Preparation of 6-Chloro-7-bromo-1,2,3,5-tetrahydroimidazo[2,1-b]quinazolin-2-one (46)

To a solution of 1.30 g (8 mmole) of anhydrous ferric chloride in 30 ml of nitromethane was added 1.30 g (5 mmole) of solid 6-chloro-1,2,3,5-tetrahydroimidazo[2,1-b]quinazolin-2-one and 0.80 g (5 mmole) of bromine. The system was stoppered, warmed to 50° in an oil bath overnight, cooled to room temperature and the solvent removed in vacuo. The resulting solid was suspended in water (50 ml), the mixture made basic (pH 10) with sodium bicarbonate and stirred at room temperature for 20 min. The solid was filtered under suction, washed with water, then isopropyl alcohol and dried yielding 1.9 g (78% yield) of a beige colored powder. Purification was effected by formation of the hydrochloride salt from acetonitrile; mp >275°.

Anal. calc'd. for $C_{10}H_7BrClN_3O.HCl$: C, 35.64; H, 2.39; N, 12.47. Found: C, 37.98; H, 2.94; N, 12.70.

Poor analysis is attributed to loss of hydrogen chloride from the salt upon drying.

EXAMPLE 25

Preparation of 6,7-Dichloro-1,2,3,5-tetrahydroimidazo[2,1-b]quinazolin-2-one (47)

Substitution in the procedure of example 24 for the bromine used therein of an equimolar quantity of chlorine produced the title product.

Anal. Calc'd. for $C_{10}H_7Cl_2N_3O.HCl$: C, 41.06; H, 2.76; N, 14.36; Cl, 36.36.

Found: C, 42.45; H, 2.95; N, 15.27; Cl, 31.66.

Poor analysis is attributed to loss of hydrogen chloride from the salt upon drying.

EXAMPLE 26

7-Amino-6-methyl-1,2,3,5-tetrahydroimidazo[2,1-b]quinazolin-2-one (48)

Substitution in the procedure of example 11 for the 7-nitro-1,2,3,5-tetrahydroimidazo[2,1-b]-quinazolin-2-one used therein of an equimolar quantity of 7-nitro-6-methyl-1,2,3,5-tetrahydroimidazo[2,1-b]quinazolin-2-one produced the title product; m.p. >260° C.

Anal. calc'd. for $C_{11}H_{12}N_4O.2HBr$: C, 34.94; H, 3.73; N, 14.82. Found: C, 35.01; H, 4.02; N, 14.69.

EXAMPLE 27

Preparation of 6,7-Dihydroxy-1,2,3,5-tetrahydroimidazo[2,1-b]quinazolin-2-one (49)

Substitution in the procedure of example 12 for the 6-methoxy-1,2,3,5-tetrahydroimidazo[2,1-b]quinazolin-2-one and 750 ml of 48% aqueous hydrobromic acid used therein of an equimolar quantity of 6,7-dimethoxy-1,2,3,5-tetrahydroimidazo[2,1-b]quinazolin-2-one and 1500 ml of 48% aqueous hydrobromic acid produced the title compound; m.p. >250° C.

Anal. Calc'd. for $C_{10}H_9N_3O_3.HCl.1/2H_2O$: C, 45.38; H, 4.19; N, 15.88. Found: C, 45.52; H, 4.04; N, 16.39.

EXAMPLE 28

Preparation of 2-methyl-6-nitrobenzyl alcohol.

To a 0° solution of 54.30 g (0.30 moles) of 2-methyl-6-nitrobenzoic acid in 500 ml of anhydrous tetrahydrofuran was added dropwise under a nitrogen atmosphere, 380 ml (0.38 moles) of a stock IM boran/THF solution at such a rate that the temperature did not exceed 5°. Upon complete addition, the ice bath was removed, the solution allowed to stir at room temperature for 14 hours, heated to reflux for 4 hrs. and then cooled to 0° in an ice bath. The reaction was quenched by the dropwise addition of 400 ml of 10% hydrochloric acid, the solution heated to reflux on a steam bath for 0.5 hrs., the THF solvent distilled at atmospheric pressure and the insoluble precipitate extracted into methylene chloride. The methylene chloride extracts were combined, washed with satd. sodium bicarbonate solution, dried ($Na_2SO_4$) and the solvent removed in vacuo affording a reddish colored semi solid. Purification was effected from 300 ml of carbon tetrachloride resulting in 41.35 g (84% yield) of yellow flakes; mp 67°–8°.

Anal. calc'd. for $C_8H_9NO_3$: C, 57.48; H, 5.43; N, 8.38. Found: C, 57.34; H, 5.42; H, 8.47.

EXAMPLE 29

Preparation of 2-Methyl-6-nitrobenzyl chloride

To a solution of 100 g (0.60 mole) of 2-methyl-6-nitrobenzyl alcohol and 5 ml of pyridine in 1.5 l of benzene was added dropwise 87 ml (1.2 mole) of neat thionyl chloride. The solution was heated to reflux for 2 hr, cooled to 0° and the reaction quenched by the slow addition of 500 ml of water. The organic phase was separated, washed with dilute sodium bicarbonate, dried ($Na_2SO_4$) and the solvent removed in vacuo. The resulting solid was crystallized from 600 ml of cyclohexane yielding 100 g (90% yield) of a colorless solid mp 55°–6°: strong lachrymator and skin irritant.

Anal. calc'd. for $C_8H_8ClNO_2$: C, 51.76; H, 4.34; N, 7.55; Cl, 19.10. Found: C, 51.99; H, 4.39; N, 7.61; Cl, 19.21.

EXAMPLE 30

Preparation of 2-bromo-6-nitrobenzyl bromide

To a solution of 57.4 g (0.27 mole) of 2-bromo-6-nitro toluene in 800 ml of carbon tetrachloride was added 52.0 g (0.29 mole) of N-bromosuccinimide and 2.5 g of benzoyl peroxide. The mixture was heated to reflux for 64 hr., cooled and filtered. Removal of the solvent in vacuo afforded 86.1 g of a viscous oil. Purification was effected by washing through alumina ($CCl_4$/ether) and crystallization from ethyl alcohol; mp 61.5°–63°.

Anal. calc'd. for $C_7H_5Br_2NO_2$: C, 28.50; H, 1.71; N, 4.75. Found: C, 28.86; H, 1.92; N, 4.85.

EXAMPLE 31

Preparation of 2,3-dimethyl-6-nitrobenzylamine

To a solution of 5.70 g (32.4 mmole) of 2,3-dimethyl-6-nitrobenzonitrile in 35 ml of anhydrous tetrahydrofuran was added dropwise under nitrogen 65 ml (65.0 mmole) of a stock IM borane/THF solution. After stirring at room temperature for 19 hr., the solution was cooled to 0° in an ice bath and the reaction quenched by the dropwise addition of 75 ml of 10% hydrochloric acid. The solution was heated to reflux for 0.5 hr., the tetrahydrofuran distilled at atmospheric pressure and the solid removed by filtration. The acidic aqueous solution was washed with ether, made basic with ammonium hydroxide and extracted with ether. The etheral extracts were combined, washed with water, dried ($K_2CO_3$) and the solvent removed in vacuo affording 3.6 g (62% yield) of a brownish colored oil. Purification could be effected by preparation of the hydrochloride salt: mp >225 w/decomp. (EtOH).

Anal. calc'd. for $C_9H_{12}N_2O_2.HCl$: C, 49.89; H, 6.05; N, 12.93; Cl, 16.36. Found: C, 50.02; H, 6.05; N, 12.94; Cl, 16.08.

EXAMPLE 32

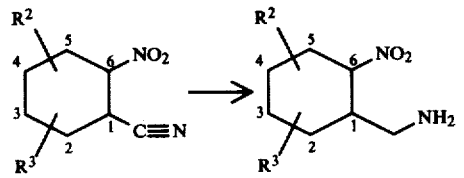

XX

Substitution in the procedure of example 30 for the 2,3-dimethyl-6-nitrobenzonitrile used therein of an equimolar quantity of the appropriately $R^2$, $R^3$-substituted 6-nitrobenzonitrile produced the compounds having formula XX in which $R^2$ and $R^3$ are as designated:

| $R^2$ | $R^3$ | % Yield | M.P. |
|---|---|---|---|
| H | 4-$CF_3$ | 28 | 190–2° C. |
| H | 4-$CH_3$ | 72 | 122–4° C. |
| 2-$CH_3$ | 4-$CH_3$ | 77* | >200° C.(d) |
| 3-$CH_3$ | 4-$CH_3$ | 59* | >230° C.(d) |
| 2-$CH_3$ | 3-$CH_3$ | 62* | >230° C.(d) |
| H | 2-Et | 59* | >230° C.(d) |
| 2-Cl | 4-Cl | 67 | oil |
| 2,3-CH=CH—CH=CH— | | 2.3 | 89–91° C. |

*as the HCl salt.

4-$CF_3$ Anal. calc'd. for $C_8H_7F_3N_2O_2$. HCL: C, 37.45; H, 3.14; N, 10.92. Found: C, 37.54; H, 3.18; N, 11.23.

2,4-diMe Anal. calc'd. for $C_9H_{12}N_2O_2$. HCL: C, 49.89; H, 6.05; N, 12.93; Cl, 16.36.

Found: C, 49.85; H, 6.03; N, 13.09; Cl, 16.25.

3,4-diMe Anal. calc'd. for $C_9H_{12}N_2O_2$.HCl: C, 49.89; H, 6.05; N, 12.93; Cl, 16.36. Found: C, 50.06; H, 6.19; N, 12.98; Cl, 15.98. 2,3-diMe Anal. calc'd. for $C_9H_{12}N_2O_2$. HCl: C, 49.89; H, 6.05; N, 12.93; Cl, 16.36. Found: C, 50.02; H, 6.05; N, 12.94; Cl, 16.08. 2-Et Anal. calc'd. for $C_9H_{12}N_2$. HCL: C, 49.89; H, 6.05; N, 12.93; Cl, 16.36. Found: C, 49.60; H, 6.11; N, 13.00; Cl, 16.26. 2,3—CH=CH—CH=CH— Anal. calc'd. for $C_{11}H_{10}N_2O_2$: C, 65.33; H, 4.98; N, 13.86. Found: C, 65.63; H, 5.24; N, 13.67.

EXAMPLE 33

Preparation of 2-Amino-6-trifluoromethylbenzyl alcohol

To 25 ml (25 mmole) of a 1M lithium aluminum hydride/tetrahydrofuran stock solution was added dropwise under a nitrogen atmosphere a solution of 5.04 g (23 mmole) of 6-trifluoromethyl anthranilic acid in 25 ml of tetrahydrofuran. After the initial vigorous reaction subsided, the mixture was heated to reflux for 18 hrs., cooled and the reaction quenched by the dropwise addition of 1.9 ml of water and 1.5 ml of 10% aqueous sodium hydroxide solution. The mixture was stirred at room temperature for 1.5 hrs., the solid filtered under suction and washed with ether. Removal of the solvent in vacuo from the filtrate afforded a crystalline solid which was purified by formation of the hydrochloride salt (MeOH/ether) yielding 4.06 g (77% yield) of a colorless solid: mp 150°-1°. Anal. calc'd. for $C_8H_8NOF_3$.HCl: C, 42.21; H, 3.98; N, 6.15. Found: C, 42.17; H, 4.28; N, 6.02.

EXAMPLE 34

Preparation of 2-Amino-6-trifluoromethylbenzyl chloride

To 4.06 g (7.8 mmole) of 2-amino-6-trifluoromethylbenzyl alcohol in a pressure bottle was added 60 ml of concentrated hydrochloric acid, the bottled stoppered and immersed in an oil bath maintained at 100°. The mixture was stirred for 1.5 hr., cooled and the precipitate filtered under suction. The colorless solid was washed with water and dried under high vacuum, yielding 3.28 g (75% yield) of a colorless solid; mp 155°-161°. The sample was used as such without further purification.

EXAMPLE 35

Preparation of 2,5-Dimethyl-6-nitrobenzyl alcohol

Substitution in the procedure of example 28 for the 2-methyl-6-nitrobenzoic acid used therein of an equimolar quantity of 2,5-dimethyl-6-nitrobenzoic acid produced the title compound in 81% yield.

EXAMPLE 36

Preparation of 2,5-Dimethyl-6-nitrobenzyl chloride

Substitution in the procedure of example 29 for the 2-methyl-6-nitrobenzyl alcohol used therein of an equimolar quantity of 2-fluoro-6-nitrotoluene produced the title product in 52% yield.

EXAMPLE 37

Preparation of 2-amino-3,6-dichlorobenzyl alcohol.

Substitution in the procedure of example 33 for the 6-trifluoromethylanthranilic acid used therein of an equimolar quantity of 3,6-dichloroanthranilic acid produced the title product in 72% yield; m.p. 96°-97° C.

Anal. calc'd. for $C_7H_7Cl_2NO$: C, 43.78; H, 3.67; N, 7.30. Found: C, 43.59; H, 3.80; N, 7.49.

EXAMPLE 38

Preparation of 2-amino-3,6-dichlorobenzyl chloride

Substitution in the procedure of example 34 for the 2-amino-6-trifluoromethylbenzyl alcohol used therein of an equimolar quantity of 2-amino-3,6-dichlorobenzyl alcohol produced the title product.

EXAMPLE 39

Preparation of 6-methyl-1,2,3,5-tetrahydroimidazo-[2,1-b]quinazolin-2-one (10)

To a 0° solution of 1.06 g (6.64 mmole) of bromine in 0.1 ml of water was added dropwise with stirring a solution of 0.367 g (7.50 mmole) of sodium cyanide in 2.6 ml of water. Upon complete addition, the reaction was stirred in the cold for 1.25 hr., removed from the ice bath, allowed to warm to room temperature (15 min) and 12 ml of absolute ethyl alcohol added. To this solution was added a solution of 1.32 g (5.97 mmole) of N-(2-amino-6-methylbenzyl)ethyl glycinate in 15 ml of absolute ethyl alcohol, the mixture allowed to stir at room temperature for 20 min. and heated slowly to reflux. After 18 hrs., of reflux, the solution was cooled and the solvent removed. To the resulting solid was added 30 ml. of water, the mixture made basic (pH-12) by the addition of concentrated ammonium hydroxide and the mixture allowed to stir for 30 mins. at room temperature. The precipitate was filtered, washed with water and dried yielding 0.93 g (77% yield) of 6-methyl-1,2,3,5-tetrahydroimidazo[2,1-b]quinazolin-2-one. Purification was effected by formation of the hydrochloride salt (30 ml of 1N HCL/1 g of product).

EXAMPLE 40

Preparation of 3-(carbethoxymethyl)-3,4-dihydro-5-methyl-4-methylene-1H-quinazolin-2-one To a solution of 22.4 g (0.15 mole) of 2-amino-6-methylacetophenone in toluene (750 ml) was added a solution of 19.4 g (0.15 mole) of ethyl isocyanatoacetate in toluene (150 ml). The system was fitted with a Dean- Stark trap and the solution heated to reflux. After the theoretical removal of water (3 hrs), the solution was cooled to 0° overnight. The solution was filtered, the precipitate washed with cold toluene and dried yielding 33.9 g (87% yield) of colorless crystals. Purification was effected by recrystallization from toluene; m.p. 151°-4°.

Anal. Calc'd. for $C_{14}H_{16}N_2O_3$: C, 64.60; H, 6.20; N, 10.76. Found: C, 64.75; H, 6.24; N, 11.04.

EXAMPLE 41

Preparation of 3-(carbethoxymethyl)-4,5-dimethyl-1,2,3,4-tetrahydroquinazolin-2-one To a suspension of 11.0 g (42 mmole) of 3-(carbethoxymethyl)-3,4-dihydro-5-methyl-4-methylene-1-H-quinazolin-2-one in 200 ml of 95% ethyl alcohol was added 1.0 g of 10% Pd/C catalyst and the mixture placed on a Paar hydrogenator. After the theoretical hydrogen absorption, the solution was filtered under suction, the catalyst washed with ethyl alcohol and the solvent removed in vacuo affording 10.9 g (98% yield) of a colorless solid identified as the title compound.

EXAMPLE 42

2-chloro-3-carbethoxymethyl-4,5-dimethyl-3,4-dihydroquinazoline

A mixture of 4.00 g (15.4 mmole) of 3-(carbethoxymethyl)-4,5-dimethyl-1,2,3,4-tetrahydroquinazolin-2-one and 40 ml of phosphorus oxychloride was immersed in an oil bath (100°) for 1.5 hr. The solution was cooled, the excess phosphorus oxychloride removed under aspirator pressure and the residue dissolved in chloroform (100 ml). The chloroform solution was washed with an aqueous saturated sodium bicarbonate solution until the wash was neutral, the chloroform extract separated, dried (Mg $SO_4$) and the solvent removed in vacuo affording 4.5 g of an oil. The spectral data was consistent with the title compound and the compound was used as such.

EXAMPLE 43

Preparation of 5,6-dimethyl-1,2,3,5-tetrahydroimidazo[2,1-b]quinazolin-2-one (50)

To a solution of 4.3 g (15.4 mmole) of 2-chloro-3-(carbethoxymethyl)-4,5-dimethyl-3,4-dihydroquinazoline in 50 ml of absolute ethanol was added a solution of 2.0 g (120 mmole) of ammonia in 25 ml of absolute ethanol, the system was stoppered and immersed in an oil bath (100°). After 16 hrs. of heating, the solution was cooled, the solvent removed in vacuo and the residue crystallized from 1N hydrochloride acid affording 2.29 g (59% yield) of yellow crystals mp 235°-40°.

Anal. calc'd. for $C_{12}H_{13}N_3O.HCl$: C, 57.26; H, 5.61; N, 16.69. Found: C, 57.08; H, 5.56; N, 16.82.

EXAMPLE 44

Preparation of 3-(carbethoxymethyl)-3,4-dihydro-6-methyl-4-methylene-1-H-quinazolin-2-one Substitution in the procedure of example 40 for the 2-amino-6-methylacetophenone used therein of an equimolar quantity of 2-amino-5-methylacetophenone produced the title compound; m.p.

Anal. Calc'd. for $C_{14}H_{16}N_2O_3$: C, 64.60; H, 6.20; N, 10.76. Found: C, 64.89; H, 6.26; N, 10.99.

EXAMPLE 45

Preparation of 3-(carbethoxymethyl)-4,6-dimethyl-1,2,3,4-tetrahydroquinazolin-2-one Substitution in the procedure of example 41 for the 3-(carbethoxymethyl)-3,4-dihydro-5-methyl-4-methylene-1-H-quinazolin-2-one used therein of an equimolar quantity of 3-(carbethoxymethyl)-3,4-dihydro-6-methyl-4-methylene-1-H-quinazolin-2-one produced the title product; m.p. 113°-114.5° C.; 98% yield.

Anal. calc'd. for $C_{14}H_{16}N_2O_3$: C, 64.10; H, 6.92; N, 10.68. Found: C, 64.56; H, 6.87; N, 10.97.

EXAMPLE 46

Preparation of 2-chloro-3-carbethoxymethyl-4,6-dimethyl-3,4-dihydroquinazoline Substitution in the procedure of example 42 for the 3-(carbethoxymethyl)-4,5-dimethyl-1,2,3,4-tetrahydroquinazolin-2-one used therein of an equimolar quantity of 3-(carbethoxymethyl)-4,6-dimethyl-1,2,3,4-tetrahydroquinazolin-2-one produced the title compound as an oil which was used as such in the next example.

EXAMPLE 47

Preparation of 5,7-Dimethyl-1,2,3,5-tetrahydroimidazo-[2,1-b]quinazolin-2-one (51).

Substitution in the procedure of example 43 for the 2-chloro-3-(carbethoxymethyl)-4,5-dimethyl-3,4-dihydro-quinazolin used therein of an equimolar quantity of 2-chloro-3-(carbethoxymethyl)-4,6-dimethyl-3,4-dihydro-quinazoline produced the title product; m.p. 265°-70° C. in 47% yield.

Anal. calc'd. for $C_{12}H_{13}N_3O.HCl$: C, 57.26; H, 5.61; N, 16.69. Found: C, 57.12; H, 5.62; N, 16.42.

EXAMPLE 48

Preparation of 5-methyl-3-(carbethoxymethyl)-1,2,3,4-tetrahydroquinazolin-2-one To a cooled solution of 15.00 g (67 mmole) of N-(2-amino-6-methyl benzyl) glycine ethyl ester in 300 ml of anhydrous tetrahydrofuran under a nitrogen atmosphere was added a solution of 11.72 g (72 mmole) of 1,1'-carbonyldiimidazole in 200 ml of anhydrous tetrahydrofuran at such a rate that the temperature did not exceed 5°. Upon complete addition, the solution was allowed to stir at room temperature for 2 hours, heated to reflux for 18 hours, cooled to room temperature and the tetrahydrofuran removed in vacuo. The residue was dissolved in methylene chloride (250 ml), washed with 5% aqueous hydrochloric acid (2×100 ml), then water (100 ml). The methylene chloride extract was dired ($Na_2SO_4$) and the solvent removed in vacuo affording 14.0 g (83% yield) of a colorless solid. purification was effected by crystallization from nitromethane; m.p.; 184°-5°.

Anal. calc'd. for $C_{13}H_{16}N_2O_3$: C, 62.89; H, 6.50; N, 11.28. Found; C, 62.85; H, 6.45; N, 11.22.

EXAMPLE 49

Preparation of
2-Chloro-3-carbethoxymethyl-5-methyl-3,4-dihydroquinazoline hydrochloride A mixture of 2.45 g (10 mmole) of 5-methyl-3-carbethoxymethyl-1,2,3,4-tetrahydroquinazolin-2-one and 20 ml of phosphorus oxychloride was immersed in an oil bath (105°-110°) for 3.5 hrs. The solution was cooled, the excess phosphorus oxychloride removed under aspirator pressure and the residue dissolved in chloroform (50 ml). ice water was added, the mixture shaken and Ice % sodium hydroxide was added dropwise to attain a pH=6. The above process was repeated until a pH=6 was maintained after shaking, the chloroform extract was separated, dried ($Na_2SO_4$) and the solvent saturated with hydrogen chloride gas and the mixture heated to gentle boiling for 10 minutes. The mixture was filtered while hot and the precipitate dried yielding 2.11 g (70% yield) of a pale yellow powder. Purification was effected by crystallization from acetonitrile; m.p. 199-201.

Anal. calc'd. for $C_{13}H_{15}ClN_2O_2HCl$: C, 51.52, H, 5.28; N, 9.24. Found: C, 51,87; H, 5.28; N, 9.27.

EXAMPLE 50

Preparation of
6-methyl-1,2,3,5-tetrahydroimidazo-[2,1-b]quinazolin-2-one (10)

To a solution of 0.60 g (2 mmole) in 20 ml of absolute ethyl alcohol was added 1.36 g (4 mmole) of a 5% ammonia/ethyl alcohol stock solution, the system stoppered and immersed in an oil bath (100°). After 16 hrs. of heating, the solution was cooled, the solvent removed in vacuo and the residue suspended in water (30 ml). The mixture was made basic (pH9) by the addition of saturated sodium bicarbonate solution, the mixture stirred at room temperature and filtered. The precipitate was washed with water, then isopropyl alcohol and dried yielding 0.32 g (80% yield) of a colorless powder. The spectral properties (ir and nmr) were identical to the known 6-methyl-1,2,3,5-tetrahydroimidazo [2,1-b]quinazolin-2-one (see example 6).

We claim:

1. The compound having the formula

I

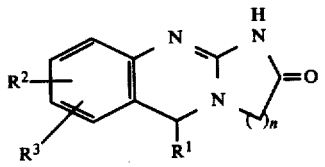

in which $R^1$ is H, phenyl or (lower)alkyl, $R^2$ and $R^3$ when different are hydrogen, chloro, bromo, fluoro, $CF_3$, $SO_3H$, hydroxy, (lower)alkyl or (lower) alkoxy, nitro, amino or phenyl, $R^2$ and $R^3$ when alike are hydrogen, bromo, chloro, fluoro, hydroxy, (lower)alkyl of 1 to 3 carbon atoms or (lower)alkoxy of 1 to 3 carbon atoms, or when taken together $R^2$ and $R^3$ are methylenedioxy or the moiety —CH=CH—CH=CH—, and n is an integer of 1 or 2; or a pharmaceutically acceptable acid addition salt thereof.

2. The compound of claim 1 having the formula

I

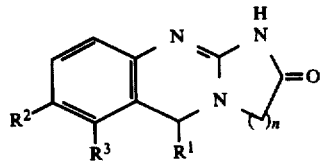

in which $R^1$ is H, phenyl or (lower)alkyl, $R^2$ and $R^3$ when different are hydrogen, chloro, bromo, fluoro, $CF_3$, $SO_3H$, hydroxy, (lower)alkyl or (lower)alkoxy or phenyl, $R^2$ and $R^3$ when alike are hydrogen, chloro, bromo, fluoro, hydroxy, (lower)alkyl of 1 to 3 carbon atoms or (lower)alkoxy of 1 to 3 carbon atoms, or when taken together $R^2$ and $R^3$ are methylenedioxy or the moiety —CH=CH—CH=C—, and n is an integer of 1 or 2; or a pharmaceutically acceptable acid salt thereof.

3. The compound of claim 1 having the formula

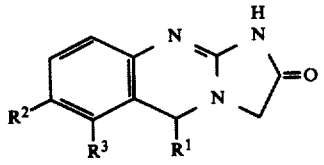

in which $R^1$ is H, phenyl or (lower)alkyl, $R^2$ and $R^3$ when different are hydrogen, chloro, bromo, $CF_3$, $SO_3H$, fluoro, hydroxy, nitro, amino, phenyl, (lower)alkyl or (lower)alkoxy, $R^2$ and $R^3$ when alike are hydrogen, chloro, bromo, fluoro, hydroxy, (lower)alkyl of 1 to 3 carbon atoms or (lower)alkoxy of 1 to 3 carbon atoms, or when taken together $R^2$ and $R^3$ are methylenedioxy or the moiety —CH=CH—CH=CH—; or a pharmaceutically acceptable acid addition salt thereof.

4. The compound of claim 3 having the formula

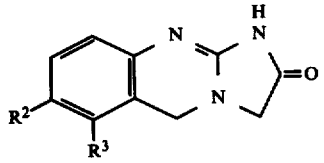

in which $R^2$ and $R^3$ when different are hydrogen, chloro, bromo, fluoro, nitro, amino, $CF_3$, $SO_3H$, hydroxy, (lower)alkoxy or (lower)alkyl, $R^2$ and $R^3$ when alike are hydrogen, chloro, bromo, fluoro, hydroxy, (lower)alkyl of 1 to 3 carbon atoms or (lower)alkoxy of 1 to 3 carbon atoms, or when taken together $R^2$ and $R^3$ are methylenedioxy or the moiety —CH=CH—CH=CH—; or a pharmaceutically acceptable acid addition salt thereof.

5. The compound of claim 2 having the formula

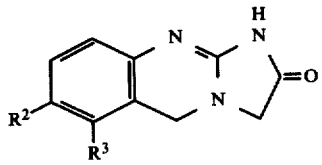

in which $R^2$ and $R^3$ are alike or different and are H, hydroxy, (lower)alkoxy of 1 to 3 carbon atoms or (lower)alkyl of 1 to 3 carbon atoms, chloro, or fluoro; or a pharmaceutically acceptable salt thereof.

6. The compound of claim 2 having the formula

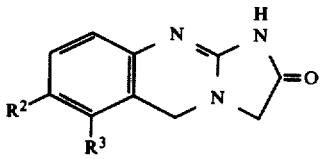

in which $R^2$ and $R^3$ are alike or different and each is H, Cl, methoxy, methyl or hydroxy; or the hydrochloride salt thereof.

7. The compound of claim 6 in which $R^2$ and $R^3$ are hydrogen; or the hydrochloride salt thereof.

8. The compound of claim 6 in which $R^2$ and $R^3$ are methoxy; or the hydrochloride salt thereof.

9. The compound of claim 6 in which $R^2$ and $R^3$ are methyl; or the hydrochloride salt thereof.

10. The compound of claim 6 in which $R^2$ is H and $R^3$ is methoxy; or the hydrochloride salt thereof.

11. The compound of claim 6 in which $R^2$ is methoxy and $R^3$ is hydrogen; or the hydrochloride salt thereof.

12. The compound of claim 6 in which $R^2$ is hydrogen and $R^3$ is methyl; or the hydrochloride salt thereof.

13. The compound of claim 6 in which $R^2$ is methyl and $R^3$ is hydrogen; or the hydrochloride salt thereof.

14. The compound of claim 4 in which $R^2$ is nitro and $R^3$ is methyl; or the hydrochloride salt thereof.

15. The compound of claim 4 in which $R^2$ and $R^3$ when taken together are —CH=CH—CH=CH—; or the hydrochloride salt thereof.

16. The compound having the formula

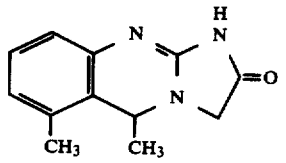

or an acid addition salt thereof.

17. The hydrochloride salt of the compound of claim 16.

18. The compound having the formula

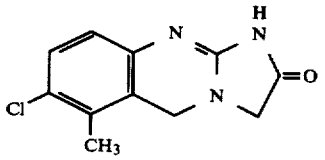

or an acid addition salt thereof.

19. The hydrochloride salt of the compound of claim 18.

*20. The compound having the formula*

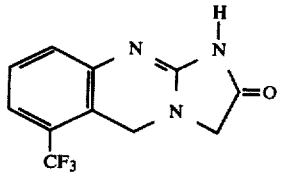

*or an acid addition salt thereof.*

*21. The compound having the formula*

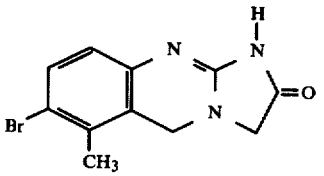

*or an acid addition salt thereof.*

*22. The compound having the formula*

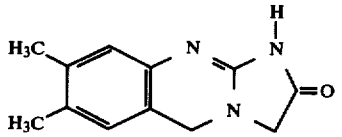

*or an acid addition salt thereof.*

*23. The compound having the formula*

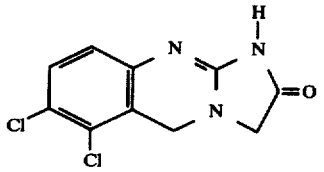

*or an acid additon salt thereof.*

*24. The compound having the formula*

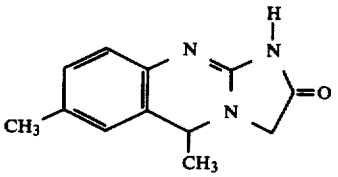

*or an acid addition salt thereof.*

*25. The compound having the formula*

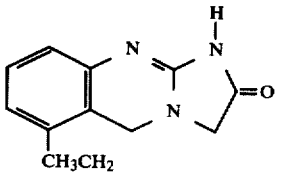

*or an acid addition salt thereof.*

* * * * *

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Title Page:

In the Title: change "TETRAHYDROIMIDEZO" to --TETRAHYDROIMIDAZO--; and change "TETRAHYDROPYIMIDO" to --TETRAHYDROPYRIMIDO--.

In the Abstract:

line 1, change "tetrahydroimidazol" to --tetrahydroimidazo--;

lines 2/3, change "tetrahydropyrimidol" to --tetrahydropyrimido--.

Col. 1, line 2, change "TETRAHYDROIMIDEZO" to --TETRAHYDROIMIDAZO--;

line 4, change "TETRAHYDROPYIMIDO" to --TETRAHYDROPYRIMIDO--;

line 55, change "diclose" to --discloses--.

Col. 4, line 22, change "devises" to --devices--.

Col. 5, line 28, change "other" to --others--;

line 61, change "$R^1$" to --N--.

Col. 8, line 35, change "are n are" to --are--;

line 36, indent "2. treating one mole...".

Col. 9, line 15, change "cluoro" to --fluoro--.

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Cols. 11/12, in Table 1, change the first equation as follows:

Change 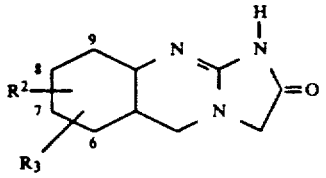 to -- 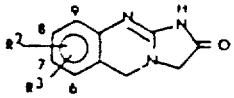 --

Cols. 11/12, in Table 1, change the second equation as follows:

Change 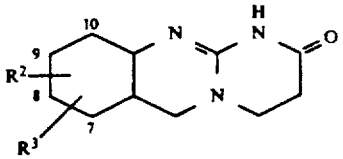 to -- 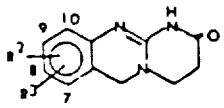 --

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Cols. 13/14, in Table 1, change the third equation as follows:

Change 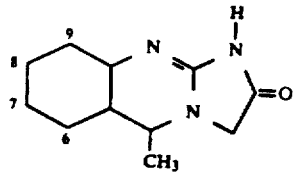 to -- 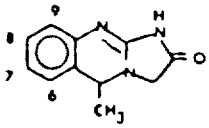 --

Col. 12, line 12, change "Hegardt, B." to --Hegardt, B.,--;

line 15, change "G. Marian" to --G., Marian,--.

Col. 15, line 20, delete "Glycinates" (second occurrence).

Col. 15, in the Table of Example 4:

Compound No. 10A, change "6-$CH_2$" to --6-$CH_3$--;

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Compound No. 11A, change "5-$CH_2$" to --5-$CH_3$--;

Compound No. 12A, change "3-$CH_2$" to --3-$CH_3$--;

Compound No. 13A, change "6-$OCH_2$" to --6-$OCH_3$--;

Compound No. 14A, change "5-$OCH_2$" to --5-$OCH_3$--;

Compound No. 15A, change "3-$OCH_2$" to --3-$OCH_3$--;

Compound No. 16A, change "5-$OCH_2$" to --5-$OCH_3$--; and change "6-$OCH_2$" to --6-$OCH_3$--;

Compound No. 17A, change "4-$OCH_2$" to --4-$OCH_3$--; and change "5-$OCH_2$" to --5-$OCH_3$--.

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Col. 16, in the Table of Example 4:

Compound No. 22A, change "6-$CH_2$" to --6-$CH_3$--;

Compound No. 27AA, change "3-$OCH_2$" to --3-$OCH_3$--;

Compound No. 28A, change "5-$OCH_2$" to --5-$OCH_3$--;

Compound No. 29A, change "$CH_2$" to --$CH_3$--;

Compound No. 30A, change "$CH_2$ to --$CH_3$--;

Compound No. 31A, change "3-$CH_2$" to --3-$CH_3$--.

Col. 16, in column 8 of the heading of the formula IV, change "G yield" to --% yield--.

Col. 22, line 61, change "aquo" to --aqueous--.

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Col. 23, line 6, change "Nitro" to --nitro--;

line 15, change "Nitro" to --nitro--.

line 45, change "cal'D" to --cal'd--; and change "$C_{10}H_9O_2$" to --$C_{10}H_9N_3O_2$--;

line 55, change "one-used" to --one used--.

Col. 24, line 20, change "EXAMMPLE 16" to --EXAMPLE 16--;

line 67, change "(Hcl)" to --(HCl)--.

Col. 25, line 10, change "$C_{12}H_{12}F_3N_2O_4$" to --$C_{12}H_{13}F_3N_2O_4$--;

line 12, after "Found: C, 42.21;" on a new line, insert

--H, 4.31; N, 8.32--;

line 42, change "etheral" to --ethereal--.

UNITED STATES PATENT AND TRADEMARK OFFICE

CERTIFICATE OF CORRECTION

PATENT NO. : Re.31,617

DATED : June 26, 1984

INVENTOR(S) : WARREN N. BEVERUNG, JR., ET AL.

It is certified that error appears in the above-identified patent and that said Letters Patent is hereby corrected as shown below:

Col. 27, line 51, change "boran" to --borane--;

line 68, change "H,8.47" to --N,8.47--.

Col. 28, line 48, change "etheral" to --ethereal--.

Col. 31, line 25, insert "Preparation of" after line 24 and before line 26.

Col. 32, line 61, change "dired" to --dried--;

line 64, change "purification" to --Purification--.

Col. 33, line 13, change "ice" to --Ice--;

line 15, change "pH=6" (both occurrences) to --pH6--;

line 25, change "51,87" to --51.87--.

Signed and Sealed this

*Fifth* Day of *November 1985*

[SEAL]

*Attest:*

*Attesting Officer*

DONALD J. QUIGG

*Commissioner of Patents and Trademarks*